(12) United States Patent
Bijari et al.

(10) Patent No.: US 11,641,985 B2
(45) Date of Patent: May 9, 2023

(54) MODULAR FLUID DISPENSING SYSTEM

(71) Applicant: ALO NEW YORK LLC, Great Neck, NY (US)

(72) Inventors: Jonathan Bijari, Great Neck, NY (US); Jason Barlia, Great Neck, NY (US); Hardeep Singh, Arlington, MA (US); Wesley Robinson, Littleton, MA (US); Matthew De Remer, Arlington, MA (US)

(73) Assignee: ALO NEW YORK LLC, Great Neck, NY (US)

( * ) Notice: Subject to any disclaimer, the term of this patent is extended or adjusted under 35 U.S.C. 154(b) by 1 day.

(21) Appl. No.: 17/229,734

(22) Filed: Apr. 13, 2021

(65) Prior Publication Data

US 2022/0322890 A1 Oct. 13, 2022

(51) Int. Cl.
| | | |
|---|---|---|
| *A47K 5/12* | (2006.01) | |
| *A61L 2/18* | (2006.01) | |
| *A47K 5/13* | (2006.01) | |
| *B67D 1/00* | (2006.01) | |
| *B67D 1/08* | (2006.01) | |

(52) U.S. Cl.
CPC ............. *A47K 5/1217* (2013.01); *A47K 5/13* (2013.01); *A61L 2/18* (2013.01); *B67D 1/0004* (2013.01); *B67D 1/0878* (2013.01); *A47K 2201/00* (2013.01); *A61L 2202/14* (2013.01); (Continued)

(58) Field of Classification Search
CPC ...... A47K 5/13; A47K 5/1217; A47K 5/1211; A47K 5/14; A47K 5/1202; A47K 5/1207; A47K 2201/00; B05B 12/122; B67D 3/0003; B67D 3/0029; B67D 3/0032

USPC .... 222/180, 181.1, 181.2, 181.3, 80–91, 52, 222/325, 333

See application file for complete search history.

(56) References Cited

U.S. PATENT DOCUMENTS

| | | | |
|---|---|---|---|
| 3,092,106 A | 6/1963 | Butler | |
| 5,836,482 A * | 11/1998 | Ophardt | ............... A47K 5/1202 222/325 |

(Continued)

FOREIGN PATENT DOCUMENTS

| | | |
|---|---|---|
| EP | 1530547 B2 | 5/2005 |
| EP | 2662008 A2 | 11/2013 |

OTHER PUBLICATIONS

International Application No. PCT/US2021/027168, International Search Report and Written Opinion dated Nov. 18, 2021, 6 pages.

(Continued)

*Primary Examiner* — Charles P. Cheyney
(74) *Attorney, Agent, or Firm* — Hard IP LLC

(57) ABSTRACT

A modular fluid dispensing system includes a rigid bottle and multiple swappable base units. The modular fluid dispensing system includes a bottle housing to house a rigid bottle, a dispenser to dispense the fluid, and an attachment mechanism to reversibly affix the modular fluid dispensing system to a support structure. The bottle housing includes a threaded fastener to form a seal with the rigid bottle and a puncturing taper to puncture a seal of the rigid bottle. The dispenser includes a pump to initiate flow of the fluid from the rigid bottle and out a nozzle in response to a command signal from a sensor. The dispenser also includes a vacuum break port to allow an external fluid to replace the fluid in the bottle and prevent formation of a vacuum.

20 Claims, 38 Drawing Sheets

(52) U.S. Cl.
CPC ..... *A61L 2202/15* (2013.01); *A61L 2202/181* (2013.01); *B67D 2210/00034* (2013.01)

(56) References Cited

U.S. PATENT DOCUMENTS

| | | | | |
|---|---|---|---|---|
| 8,550,378 | B2* | 10/2013 | Mazooji | B05B 9/0861 222/88 |
| 8,646,655 | B2* | 2/2014 | Wegelin | A47K 5/1217 222/23 |
| 8,662,356 | B2* | 3/2014 | Padain | A47K 5/1217 222/481.5 |
| D732,309 | S | 6/2015 | Lisbona Vives | |
| 9,204,765 | B2* | 12/2015 | McNulty | B05B 11/3087 |
| D747,118 | S | 1/2016 | Lisbona Vives | |
| D873,581 | S | 1/2020 | Lisbona Vives | |
| 10,588,467 | B2 | 3/2020 | Yang | F04B 43/026 |
| 2012/0111885 | A1* | 5/2012 | Binderbauer | A47K 5/1214 222/113 |
| 2012/0187146 | A1 | 7/2012 | Chopra | |
| 2014/0138402 | A1* | 5/2014 | Warren | B05B 9/0403 222/2 |
| 2015/0083754 | A1* | 3/2015 | Proper | B67D 3/0029 222/180 |
| 2016/0228897 | A1* | 8/2016 | Buckalter | A47K 5/1204 |
| 2019/0133384 | A1* | 5/2019 | McNulty | A47K 5/1211 |
| 2020/0197966 | A1* | 6/2020 | Marshall | A47K 5/14 |
| 2021/0076882 | A1* | 3/2021 | Fauconnier | A47K 5/1204 |

OTHER PUBLICATIONS

Touchland, "Kub Premium Kit Pure White|Touchland," URL: https://touchland.com/products/white-kub-premium-package, Jan. 7, 2021, pp. 1-8.

Staples, "Purell ES1 Dispenser Starter Kit, Push-Style Hand Sanitizer Dispenser, 450 mL Refill Included, Graphite (4424-D6)," URL: https://www.staples.com/purell-es1-starter-kit-70-alcohol-gel-hand-sanitizer-dispenser-with-refill-450ml-4424-d6/product_24467075?ci_src=17588969&ci_sku=24467075&KPID=24467075&cid=PS:CRL:GS:SBD:PLA:Fac&gclid=CjwKCAiAyc2BBhAaEiwA44-wW82z4U_dNdLbudMmZKCEwynCqZaUWbLxjSIVf1sdUvUHZCP4gJXMdhoCtC0QAvD_BwE, 2021, pp. 1-4.

Touchland, "Shop Kub—Touchland," URL: https://touchland.com/collections/shop-kub, Jan. 7, 2021, pp. 1-7.

Totalrestroom, "Vista Hand Sanitizer . . . " URL: https://www.totalrestroom.com/products/vista-hand-sanitizer-stand-w-automatic-dispenser-and-purell-12-6-oz-pour-bottle-refills?dfw_tracker=90000-C3066934&utm_source=google&utm_medium=surfaces&utm_campaign=shopping%20feed&utm_content=free%20shopping%20clicks&gclid=CjwKCAiAyc2BBhAaEiwA44-wW8mdvsVqBaYMZvoC4kCzs1C7WFO-hwp6fGJUvKWxwOfApGQU5LgdpBoC-QoQAvD_BwE, 2020, pp. 1-5.

* cited by examiner

MODULAR FLUID DISPENSING SYSTEM

TECHNICAL FIELD

This disclosure relates generally to a modular fluid dispensing system, and more particularly to a modular fluid dispensing system which includes a rigid bottle and multiple swappable base units to dispense liquids.

BACKGROUND

Use of hand sanitizing solution helps prevent the spread of germs. Hand sanitizing solution is especially useful to people as an alternative to washing their hands. In areas that may have high levels of traffic, hand sanitizing dispensers may be placed to encourage people to disinfect their hands. These hand sanitizing dispensers include manually operated dispensers that pump out hand sanitizing solution upon a user pushing against a lever which causes liquid hand sanitizing solution to dispense onto the user's hand. Other types of hand sanitizing dispensers include ones that dispense liquid hand sanitizing solution upon a senser sensing a user's hand being waived underneath the dispensers or upon a user pressing against a button.

These hand sanitizing dispensers may be wall mounted while others may be placed on the floor or a table. Transportation or movement of such hand sanitizing dispensers is not easy and once a hand sanitizing dispenser is mounted or placed, it is not usually movable. Another disadvantage of wall mounted dispensers is that people may not notice the dispenser or the dispensers may not be placed in an optimal location where people can easily use them.

Free-standing hand sanitizing dispensers may be bulky and may also be difficult to move. Furthermore, such dispensers that are placed in heavy use areas often require refilling of hand sanitizing solution. Unless employees are constantly monitoring and replacing the collapsible bags refills of hand sanitizing solution, the dispensers remain empty. This can be frustrating for users who wish to disinfect their hands.

SUMMARY

The following presents a simplified summary of various aspects of this disclosure in order to provide a basic understanding of such aspects. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

In an aspect of the present disclosure, a modular fluid dispensing system which includes a rigid bottle and multiple swappable base units to dispense liquids is provided. A bottle housing to house a bottle may be affixed to a dispenser to dispense the fluid in the bottle. The bottle housing may include a removable lid. The bottle may be installed onto a threaded fastener including a puncturing taper to break the seal of the bottle. A pump may be used in the dispenser to initiate flow from the bottle and out through a nozzle in response to a command received from a sensor. The dispenser may include a vacuum break port to replace the fluid in the bottle during dispensing to prevent formation of a vacuum. An attachment mechanism may reversibly affix the modular fluid dispensing system to one of several support structures.

In another aspect of the present disclosure, the removable lid may include a reverse threaded fastener to frustrate attempts to pilfer the bottle.

In another aspect of the present disclosure, the fluid may be any of a variety of fluids, such as a sanitizing solution, a liquid soap, a lotion, a shampoo, a conditioner, a beverage, or a condiment, according to the needs of the intended user.

In another aspect of the present disclosure, light emitting diodes (LEDs) are provided to convey information to a user, illuminate an area for safety, or for aesthetic purposes.

In another aspect of the present disclosure, power for the electrical components of the modular fluid dispensing system may be provided by an electrical battery or an adapter to connect to an electrical receptacle.

In another aspect of the present disclosure, the dispenser uses a light sensor to detect and activate in response to the presence of a hand of a user to enable touch-free operation.

In another aspect of the present disclosure, the modular fluid dispensing system may be reversibly affixed to a wall or to a base unit for use on a table or for use on a floor.

In another aspect of the present disclosure, concave surfaces are provided on the bottle as finger grooves to allow a user to rotate the bottle with their fingers.

In another aspect of the present disclosure, a specific thread angle is provided for the threaded fastener according to design requirements.

In another aspect of the present disclosure, a captive screw assembly is provided to reversibly affix the attachment mechanism to a support structure without dropping or losing the screw.

In another aspect of the present disclosure, a drip tray is provided to catch drips from the nozzle or running off the hands of a user. The drip tray may be removable for cleaning or replacement.

In another aspect of the present disclosure, an additional sensor is provided to detect movement of the fluid such that the volume of fluid dispensed may be directly measured.

In another aspect of the present disclosure, an additional sensor is provided to detect the current draw of the pump such that a change in current draw may be used to determine when the bottle is empty.

In another aspect of the present disclosure, a selector switch is provided to allow a user to select from several pre-configured dispensing modes.

BRIEF DESCRIPTION OF THE DRAWINGS

The present disclosure is illustrated by way of example, and not by way of limitation, in the figures of the accompanying drawings, in which.

DETAILED DESCRIPTION

Figure 1:
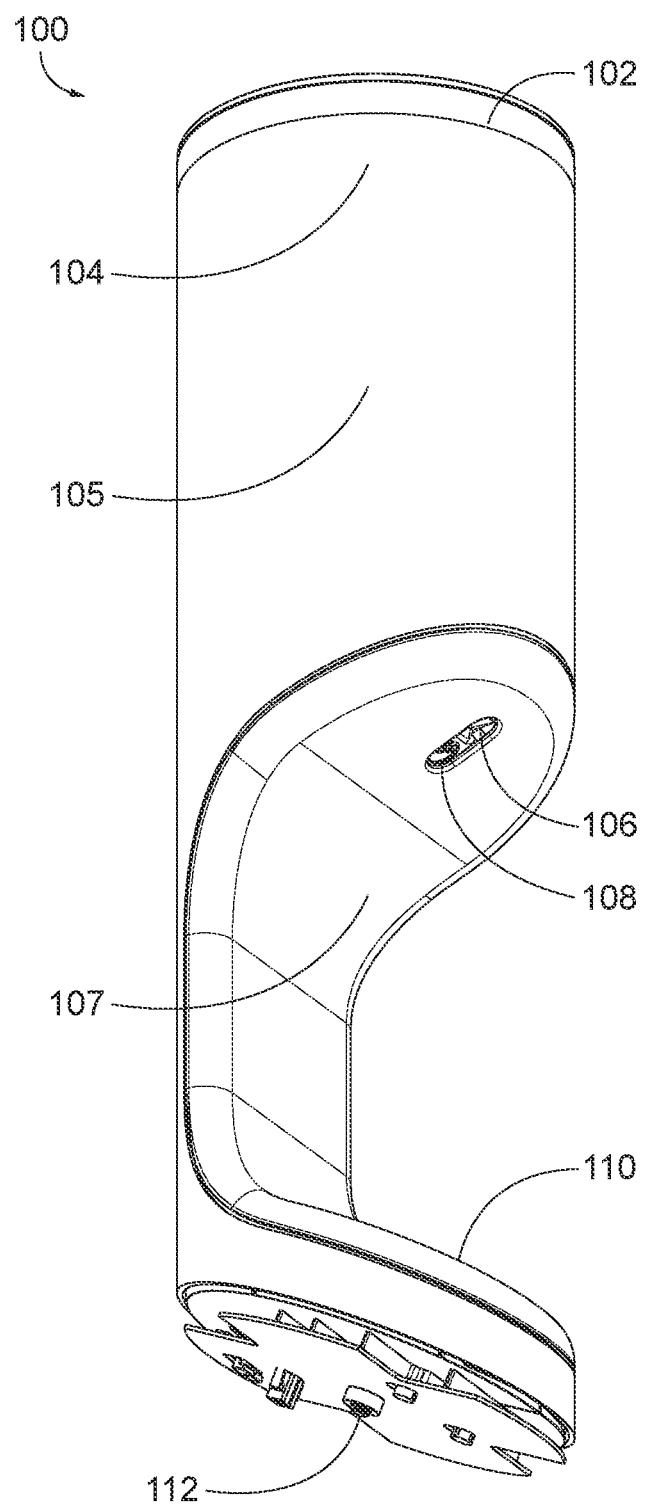
FIG. 1 illustratively depicts a modular fluid dispensing system, in accordance with an implementation of the disclosure.

Before the present subject matter is described in detail, it is to be understood that this disclosure is not limited to the particular implementations described, as such may vary. It should also be understood that the terminology used herein is to describing particular implementations only, and is not intended to be limiting, since the scope of the present disclosure will be limited only by the appended claims. While this disclosure is susceptible to different implementations in different forms, there is shown in the drawings and will here be described in detail a preferred implementation of the disclosure with the understanding that the present disclosure is to be considered as an exemplification of the principles of the disclosure and is not intended to limit the broad aspect of the disclosure to the implementation illustrated. All features, elements, components, functions, and steps described with respect to any implementation provided herein are intended to be freely combinable and substitutable with those from any other implementation unless otherwise stated. Therefore, it should be understood that what is illustrated is set forth only for the purposes of example and should not be taken as a limitation on the scope of the present disclosure.

In the following description and in the figures, like elements are identified with like reference numerals. The use of "e.g.," "etc.,", "or" and "the like" indicates non-exclusive alternatives without limitation, unless otherwise noted. The use of "having", "comprising", "including" or "includes" means "including, but not limited to," or "includes, but not limited to," unless otherwise noted.

Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" can refer, in one implementation, to A only (optionally including entities other than B); in another implementation, to B only (optionally including entities other than A); in yet another implementation, to both A and B (optionally including other entities). These entities may refer to elements, actions, structures, steps, operations, values, and the like.

People in the course of their daily lives use many varieties of fluids. Water, for instance, is used for such purposes as drinking, cooking, and washing. Individuals may apply fluids such as lotions, shampoos, and/or conditioners to their bodies. Foods commonly include added fluids such as oils, sauces and syrups. For some fluids, it is particularly convenient to maintain a volume and automatically dispense the fluid in a pre-determined portion of that volume. For example, mechanical dispensers that contain hand sanitizing solutions may allow users to receive a pre-determined volume of the hand sanitizing solution.

A variety of challenges present themselves, however, when mechanical dispensers are not maintained. First, when the dispensing liquid needs to be refilled, a user must refill the liquid upon manual inspection which requires constant monitoring of the dispenser. Tracking the refill status of a dispenser may prove even more challenging when there are a large quantity of dispensers in use, particularly if the dispensers are distributed across a wide area. Second, flexibility in what fluid will be dispensed by a dispenser is limited. For instance, if a new hand sanitizing solution is to be deployed, such solution must be contained in the same form as the old hand sanitizing solution. Typically, the solution is prefilled in a collapsible plastic pouch or bag and the bags can only be unique to a compatible manufacturer of the dispenser and therefore, may not be universally compatible. Finally, flexibility in positioning a dispenser may be limited. Users may not be provided with the option to mount the dispenser on a wall and also allow the dispenser to be free-standing (e.g., allow placement of the dispenser on a desk, a table, the floor, or any surface). The present disclosure addresses these challenges by providing a modular fluid dispensing system that can be mountable or free-standing and one that can use an easily refillable bottle that holds the fluid. Specifically, the modular fluid dispensing system includes a rigid bottle and vacuum break port that provides ease of use and ease of refill.

Additionally, the dispensing system is modular such that it can be wall mounted or free-standing and may toggle between various implementations.

Various aspects of the above referenced apparatus are described in detail herein below by way of examples, rather than by way of limitation.

FIG. 1 illustratively depicts a modular fluid dispensing system 100. The modular fluid dispensing system 100 includes a bottle housing 105, a dispenser 107, and an attachment mechanism 112. The bottle housing 105 includes a removable lid 102 and one or more light emitting diodes (LEDs) 104. The dispenser 107 includes a sensor 106, a nozzle 108 and a removable face plate 110. The bottle housing 105 and the dispenser 107 together form the body of the modular fluid dispensing system 100. The removable lid 102 and the removable face plate 110 may be removed, enabling the user to access various internal components for maintenance, installation, and fluid refills.

The bottle housing 105 may include one or more cylindrical wall sections encircling an internal cavity to enclose a bottle (not shown). For example, a cylindrical wall section of the bottle housing 105 may be constructed of a material such as plastic, metal, paper/cardboard, glass, or combinations thereof. A cylindrical wall section may be of a thickness between 0.2 cm-1.5 cm or another thickness. A cylindrical wall section of the bottle housing 105 may also include one or more gaps to accommodate additional structural or functional components.

As described above, the removable lid 102 may be temporarily and/or removably affixed to the top of the bottle housing 105 to protect and visually hide the contents of the bottle housing 105. In an implementation, the removable lid 102 includes a threaded fastener to couple with the bottle housing 105. The removable lid 102 may couple with the bottle housing 105 in response to rotating the removable lid 102 in a counter-clockwise direction. As rotating the removable lid 102 in a counter-clockwise direction to tighten the seal is the reverse of standard threading, it is anticipated that this may frustrate some attempts to pilfer the bottle (not shown) and thus deter theft of the bottle (not shown). In another implementation, the removable lid 102 may be removably affixed to the bottle housing 105 using a clip or a sliding lock mechanism. In yet another implementation, the lid may be permanently affixed to the bottle housing 105.

The dispenser 107 is configured to dispense the fluid and is affixed underneath the bottle housing 105. The dispenser 107 includes a curved surface to support the weight of the bottle housing 105 while providing access underneath the bottle housing 105. The sensor 106 is affixed underneath the bottle housing 105 at the top of the dispenser 107 and is used to initiate the dispensing of the fluid. For example, a user may place his/her hand underneath the dispenser 107 in order to receive the liquid. The sensor 106 detects the presence of a hand of the user by sensing the reflection of skin in the infrared spectrum. In other implementations, the sensor 106 may utilize a different spectrum of light or sound and may be configured to detect the presence of other activating bodies. In another implementation, a button (not shown) may be provided for the user to initiate the dispensing of the fluid from the modular fluid dispensing system 100. Other forms of accepting an input command from a user to dispense liquid may be used.

In an implementation, the LEDs 104 may be affixed near the top of the bottle housing 105, below the removable lid 102. In other implementations, the LEDs 104 may be placed in any location. Multiple LEDs are affixed inside the bottle housing 105 and the light emitted thereby is refracted out of the ring to provide a more aesthetically pleasing light display. The LEDs 104 may be capable of emitting light in more than one color, and the varieties of color are used for decorative and/or informational purposes.

The LEDs 104 may illuminate in a color pattern in response to a signal from a control unit (not shown). Suppose that the dispenser 107 encloses a bottle (not shown) which contains only air. It may be advantageous to alert a user that the bottle does not contain the fluid normally dispensed by the dispenser 107. In an implementation, a color pattern may be displayed by the LEDs 104 to alert a user of the status of the dispenser 107.

The LEDs 104 may also be used to provide ambient lighting or provide light in a dark area in an aesthetically appealing manner. In addition, a display unit (not depicted) may be included which may provide a textual and/or pictorial and/or video message.

The nozzle 108 is also affixed underneath the bottle housing 105 and provides the dispensing point for the fluid. The diameter of the nozzle 108 is determined by the desired flowrate and the type and viscosity of the fluid to be dispensed by the modular fluid dispensing system 100. In an implementation, the fluid is a liquid hand sanitizing solution. In other implementations, the fluid may be a sanitizing solution, a liquid soap, a lotion, a shampoo, a conditioner, a beverage, and/or a condiment.

The attachment mechanism 112 may be located on an exterior surface of the body. The attachment mechanism 112 may reversibly affix the body to a support structure to support the modular fluid dispensing system 100. The attachment mechanism 112 may be located on one or both of the following locations: underneath the dispenser 107 and/or on the back of the dispenser 107. By affixing an attachment mechanism 112 underneath the dispenser 107, the modular fluid dispensing system 100 may be reversibly affixed to a base unit for display and use on one of a table or a floor. By affixing an attachment mechanism 112 to the back of the dispenser 107, the modular fluid dispensing system 100 may be reversibly affixed to a wall.

The modular fluid dispensing system 100 may be constructed from any suitable rigid material or a combination of materials. In an implementation, the external surface of the modular fluid dispensing system 100 is a brushed metal. In another implementation, the external surface of the modular fluid dispensing system 100 may be a thermoplastic or glass. Individual components may be constructed from the same material as the external surface of the modular fluid dispensing system 100 or from different materials and are described in greater detail in following paragraphs.

Figure 2:
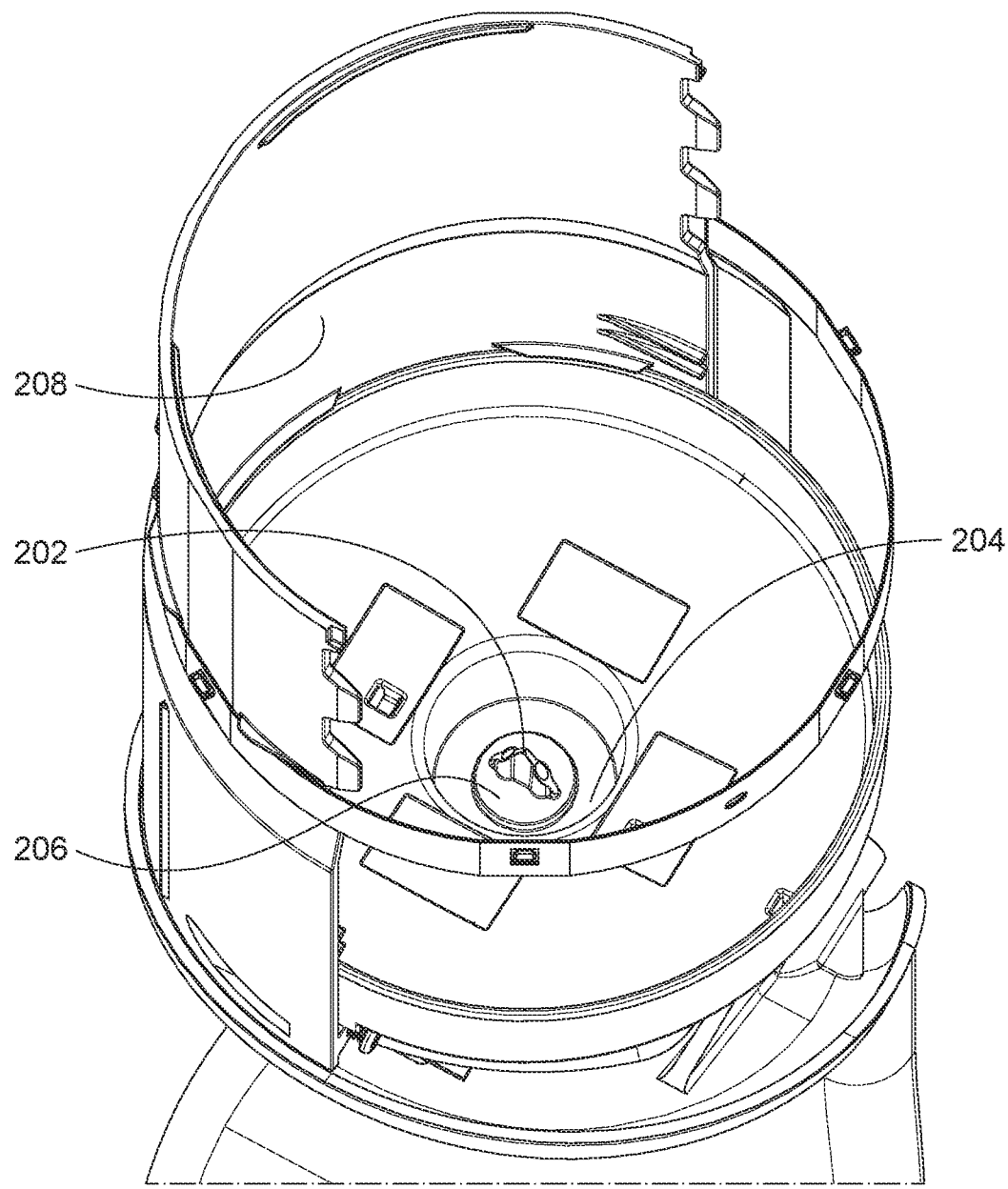
FIG. 2 illustratively depicts an internal view of a bottle housing, in accordance with an implementation of the disclosure.

FIG. 2 illustratively depicts an internal view of a bottle housing 200. The bottle housing 200 includes a puncturing taper 202, a threaded fastener 204, a fluid port 206, and a bottle housing shell 208. As discussed above, the bottle housing shell 208 may be constructed from the same material or different materials from the external surface of the modular fluid dispensing system 100. In an implementation, the bottle housing shell 208 is constructed from a thermoplastic, a metal, a glass, and/or another material.

The bottle housing 200 may house a bottle (not shown) in a static position where a mouth of the bottle is pointed downwards to allow gravity draining of the bottle. The threaded fastener 204 is affixed to the bottom of the bottle housing 200 and provides the mating point for a bottle with complementary threads for forming a fluid seal between the bottle and the fluid port. In an implementation, the threaded fastener 204 forms a fluid seal in response to the bottle being rotated into position, such that the fluid inside the bottle is retained by the threaded fastener. In an implementation, the fluid seal forms in response to rotating the bottle in a counter-clockwise direction. As rotating the bottle (not shown) in a counter-clockwise direction to tighten the seal is the reverse of standard threading, it is anticipated that this may frustrate some attempts to pilfer the bottle and thus deter theft of the bottle.

The puncturing taper 202 is affixed to the bottom of the bottle housing 200, central to the threaded fastener 204 and may puncture a membrane seal of the bottle. Refill bottles may be sealed across the mouth with a membrane seal to maintain fluid quality and prevent leakage. The membrane seal may include multiple layers and may include one or more of foil, thermoplastic, and/or paper. The puncturing taper 202 is rigid and configured with a sharp point, such that as the bottle is lowered while threading onto the threaded fastener 204, the puncturing taper 202 punctures the membrane seal of the bottle and initiates fluid flow from the bottle (not shown). In an implementation, the puncturing taper 202 may be constructed from a thermoplastic. In another implementation, the puncturing taper 202 may be constructed from a metal or other material or combination of materials.

The fluid port 206 provides a fluid connection between the bottle and the dispenser (not shown) to permit flow of a fluid at least one of in or out of the bottle. In an implementation, the fluid port 206 includes a first opening of a first fluid channel and a first opening of a second fluid channel. In an implementation, the fluid port 206 is integrated with the puncturing taper 202 and the first opening and second opening enter a fluid connection with the fluid inside the bottle (not shown) as the bottle is lowered while threading onto the threaded fastener 204. As will be described below, a pair of fluid channels is advantageous as it allows for active fluid replacement while pumping.

Figure 3A:
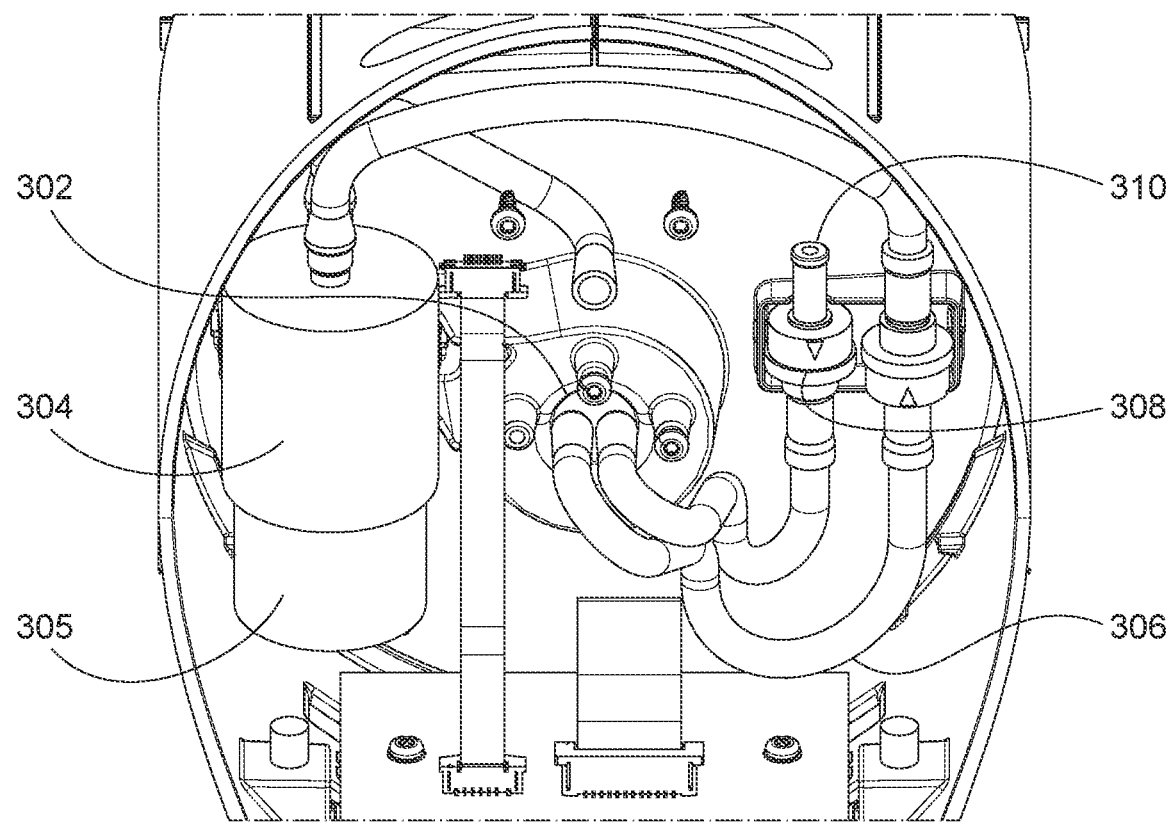
FIG. 3A illustratively depicts an internal view of a dispenser upper section, in accordance with an implementation of the disclosure.

FIG. 3A illustratively depicts an internal view of a dispenser upper section 300. The dispenser upper section 300 includes a fluid port 302, a pump 304, a tubing system 306, and a vacuum break port 310. The tubing system 306 includes a one-way valve 308. The pump 304 includes a pump motor 305. The dispenser upper section 300 is affixed underneath the bottle housing 105. The pump 304, tubing system 306, one-way valve 308, and vacuum break port 310 are affixed to the top of the dispenser upper section 300. In an implementation, the fluid port 302 includes a second opening of the first fluid channel and a second opening of the second fluid channel. The fluid port 302 may be the same as the fluid port 206 as described in FIG. 2 above.

The pump 304 may initiate flow of the fluid in response to receiving the command from a sensor. Flow work is produced by the pump 304 by translating rotation of a shaft (not shown) into one of a positive displacement, a centrifugal force, or an axial force. In an implementation, the pump 304 is a centrifugal pump. In another implementation, the pump 304 is a peristaltic positive displacement pump.

The shaft (not shown) of the pump 304 is driven by the pump motor 305. The pump motor 305 may be an electrically powered motor, consisting of an electromagnetic stator surrounding a rotor. The pump motor 305 may be either brushed or brushless. The pump motor 305 may operate on either alternating current (AC) or direct current (DC) electrical power to produce rotation. In an implementation, when a user places their hand in front of the dispenser, a sensor (not shown) sends a signal to the pump motor 305, the pump motor 305 rotates in response to the signal, the pump 304 is driven by the rotation of the pump motor 305, and flow work is produced by the pump 304 in the fluid to be dispensed.

In addition, the pump motor 305 may be equipped with one or more sensors to detect the current draw of the pump motor 305 while in operation. A control unit (not shown) uses the current draw of the pump motor 305 while in operation to note a change in the viscosity of the fluid passing through the pump 304. As each bottle will contain a homogenous fluid, a change in the viscosity of the fluid passing through the pump 304 would indicate that the bottle (not shown) is empty and the pump 304 is attempting to move air. Thus, the control unit would be alerted by the pump 304 that the fluid is depleted (or its fill level is getting low) and the control unit can send a command to the LEDs 104 to flash or depict a particular visual indicator to let users know that the fluid should be refilled. The control unit may also communicate with a server (e.g., a remote server, a local server, an email server, a web server, short message service (SMS) messaging system, etc.) using wired and/or wireless communications.

In addition, the control unit may include or be connected to a Bluetooth device, a WiFi-enabled device, and/or a device that can communicate via cellular signals. For example, there may be a device with a subscriber identification module (SIM) card and/or a wireless transmitter/receiver connected thereto that is part of the control unit or is connected to the control unit. The control unit may therefore connect to or otherwise communicate remotely with external devices (e.g., mobile devices, computers, servers, etc.) that are running an app. The app. may inform a user of the external device when one of the modular fluid dispensing systems 100 needs to be refilled via submission of an email, text message or other alert. Suppose that the user manages multiple systems. Having the app. inform the user when one or multiple modular fluid dispensing systems 100 require liquid refills would save a user time from having to manually check each unit. Additionally, modular fluid dispensing systems 100 may include a global positioning system (GPS) device that can track the location of the device. The control unit may also transmit the GPS location to the app. As an alternative to the app., the control unit may correspond directly with a remote server, a local server, an email server, a web server, short message service (SMS) messaging system, etc. via wired and/or wireless communications.

The tubing system 306 may form a fluid connection between the fluid port 302, the pump 304, and the nozzle (not shown). The tubing system 306 further forms a fluid connection between a vacuum break port 310 and the fluid port 302. In an implementation, one or more one-way valves 308 are included within the tubing system 306. The tubing system 306 may be constructed from either rigid or flexible tubing, or a combination thereof in segments, according to design specifications. In an implementation, the tubing system 306 is constructed from flexible rubber tubing. In another implementation, the tubing system 306 is constructed from rigid plastic tubing. In a third implementation, the tubing system 306 is constructed from semi-rigid metal tubing.

The tubing system 306 includes a vacuum break port 310 which may permit air into the bottle (not shown) such that as the pump 304 initiates flow of the fluid from the bottle and out through the nozzle (not shown) the fluid flowing out of the bottle is replaced with the air. The vacuum break port 310 includes a first opening which may permit ingress of a fluid and a second opening which may be connected to the tubing system 306. The second opening of the vacuum break port 310 is connected to a first opening of the tubing system 306, and a second opening of the tubing system 306 is connected to the second opening of a fluid channel in the fluid port 302, forming a continuous fluid connection between the first opening of the vacuum break port 310 and the bottle (not shown). The first opening of the vacuum break port 310 may permit ingress of atmospheric air. In another implementation, the first opening of the vacuum break port 310 may permit ingress of a fluid (e.g., carbon dioxide, nitrogen oxide, or argon) from an external source for pressurized dispensing or inert blanketing of the bottle. In another implementation, the first opening of the vacuum break port 310 may be configured to permit ingress of the same fluid as is contained in the bottle such that the bottle may be refilled.

The tubing system 306 further includes a one-way valve 308 which may prevent the fluid from flowing out of the vacuum break port 310. The one-way valve 308 is configured to open only if pressure at the second opening of the vacuum break port 310 is greater than the pressure inside the bottle (not shown) and remain shut otherwise. Including a one-way valve 308 before the vacuum break port 310 is advantageous for reducing egress of the fluid from the vacuum break port 310. In an implementation, the one-way valve 308 includes a pair of sealing surfaces which may separate in response a positive differential pressure in the expected flow direction and form a fluid seal in response to a negative differential pressure in the expected flow direction. In one example, one-way valves 308 may be duck one-way valves or other one-way valves. In another implementation, the one-way valve 308 includes a spring which may prevent flow until a minimum differential pressure is achieved. In an implementation, the one-way valve 308 is located within the flow path between the second opening of the vacuum break port 310 and the second opening of a fluid channel in the fluid port 302. In another implementation, the one-way valve 308 is integrated with one of either the vacuum break port 310 or the fluid port 302.

The tubing system 306 may include one or more additional one-way valves 308. The tubing system 306 includes a one-way valve 308 located within the flow path between the bottle (not shown) and the nozzle (not shown). Including a one-way valve 308 before the nozzle may be advantageous for preventing contamination of the fluid remaining in the bottle due to backflow. For example, a one-way valve 308 may be integrated in between the second opening of a fluid channel in the fluid port 302 and the pump 304.

Figure 3B:
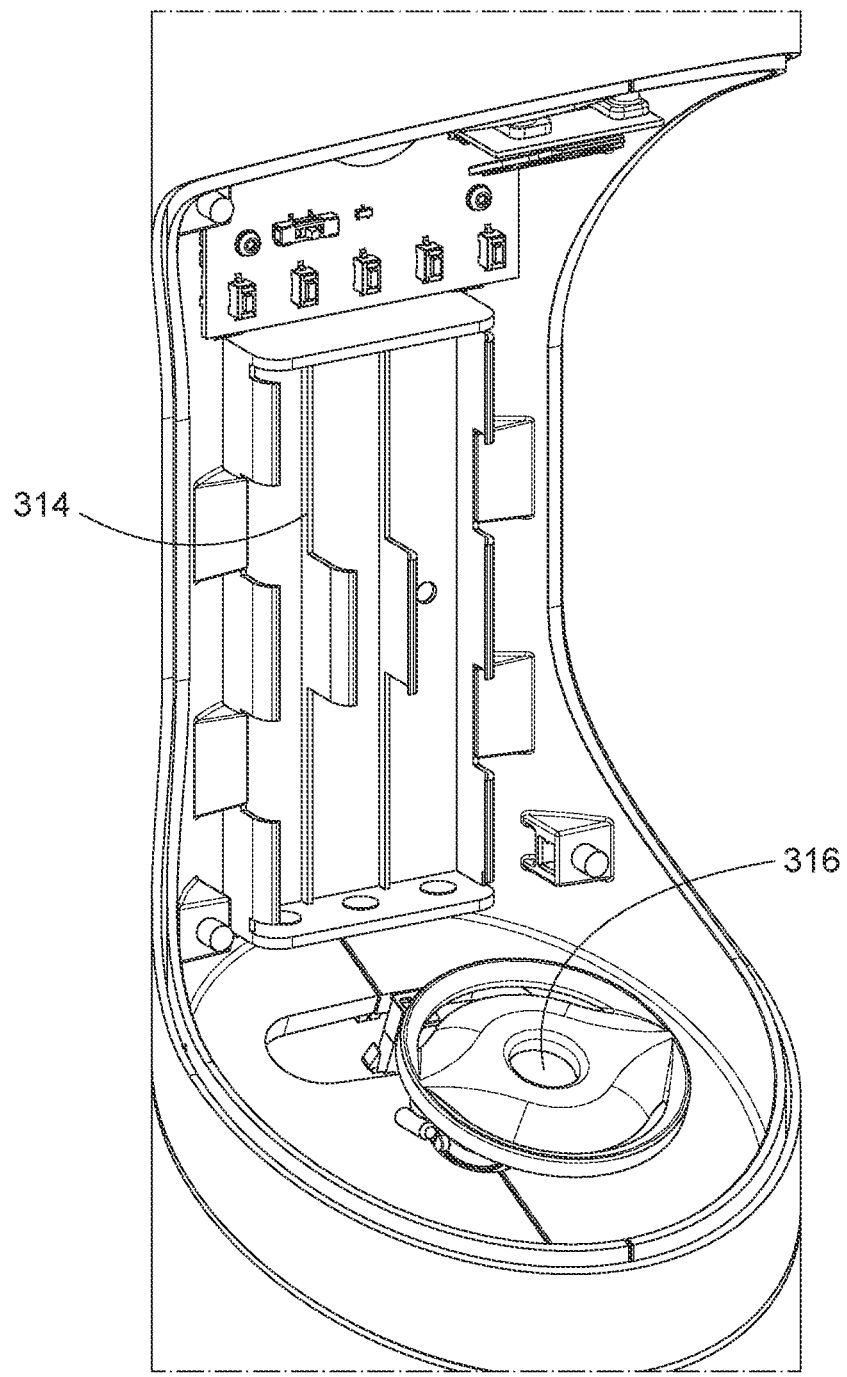
FIG. 3B illustratively depicts an internal view of a dispenser lower section, in accordance with an implementation of the disclosure.

FIG. 3B illustratively depicts an internal view of a dispenser lower section 312. The dispenser lower section 312 includes an electrical power supply 314 and a drip tray 316. The dispenser lower section 312 is located underneath the dispenser upper section 300 as described above.

The dispenser 107 as described above includes one or more electromechanical components (not shown) and/or one or more control units (not shown). Therefore, an electrical power supply 314 is included to power the dispenser 107 and all components requiring electrical power therein. The electrical power supply 314 may be an electric battery compartment that may house an electrical battery or an adapter which may connect to an electrical receptacle.

As described above, the dispenser 107 may include a removable face plate 110. The removable face plate 110 may at least partially cover the electrical power supply 314, such that in response to removing the removable face plate 110 the electrical power supply 314 is at least partially uncovered. Suppose that a modular fluid dispensing system 100 houses an electrical battery and a user wishes to inspect and/or replace the electrical battery. By removing the removable face plate 110, the user may gain the access required to inspect and/or replace the electrical battery. The electrical battery may include a plurality of cells in any combination of primary and/or rechargeable cells.

As described above, various known dispensers are typically either wall mounted or free-standing. However, the present dispensing system is customizable and is modular in nature and can toggle between various forms via the attachment mechanism described herein. Suppose that a user wishes to place dispensers containing a hand sanitizing solution in each bathroom in an office building, in the hallways of the office building, and on selected tables/desks (such as the reception desk). The dispensing system can be placed as free-standing or may be wall mounted and can change forms (from free-standing to wall-mounted and vice versa). The dispensing systems may be temporarily affixed to each of the walls of the bathrooms and to base units for hallway floors and tables and can be moved and change form as needed.

Referring again to FIG. 3B, the dispenser lower section 312 includes a first male connection or a first female connection that may couple to one of a second male or a second female connection of a base unit (not shown) at a thread angle. Base units will be described in greater detail in following paragraphs.

The removable face plate 110 may at least partially cover the attachment mechanism (not shown), such that in response to removing the removable face plate 110 the attachment mechanism is at least partially uncovered.

The attachment mechanism (not shown) may at least temporarily affix the modular fluid dispensing system 100 to a support structure (not shown). The support structure may be a wall or a base unit configured for placement on a floor or a table. The attachment mechanism may include one or more hooks, posts, slots, tabs, screws, pins, and/or bolts. In an implementation, the attachment mechanism includes one or more captive screw assemblies that provide that the captive screw assembly is retained in its position when unthreaded. A captive screw assembly may include one or more washers. In another implementation, the attachment mechanism includes one or more positioning posts including a first male connection or a first female connection that may couple to one of a second male or a second female connection of a base unit.

The dispenser lower section 312 further includes a drip tray 316. Suppose that a user activates the modular fluid dispensing system 100 by placing a hand in sensory range of the sensor 106, but withdraws the hand while dispensing is still in progress. The drip tray 316 may trap and/or retain drops of a fluid from the nozzle 108. The drip tray 316 may also trap and/or retain drops of a fluid from a hand of a user. By directing drips to the drip tray 316, a user may easily clean the modular fluid dispensing system 100.

The drip tray 316 may be removable from the dispenser lower section 312 for washing, sanitizing, or replacement. The drip tray 316 may be integrated with the removable face plate 110 described above. The drip tray 316 may be constructed from any of a metal, a plastic, a glass, another material, or a combination thereof.

Figure 4:
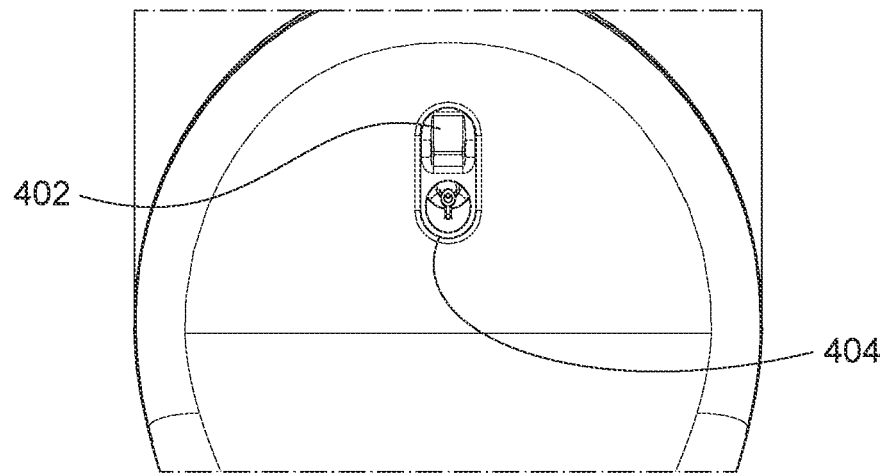
FIG. 4 illustratively depicts an external view of a modular fluid dispensing system, in accordance with an implementation of the disclosure.

FIG. 4 illustratively depicts an external view of a modular fluid dispensing system 400. The modular fluid dispensing system 400 includes a sensor 402 and a nozzle 404. The sensor 402 and the nozzle 404 are affixed to the dispenser lower section 312 as described above. The sensor 402 may be the same as the sensor 106 as described in FIG. 1 above. The nozzle 404 may be the same as the nozzle 108 as describe in FIG. 1 above.

It may be advantageous to automate the dispensing of fluid from the modular fluid dispensing system 400. Therefore, the modular fluid dispensing system 400 may allow a user to initiate a cycle of dispensing. A sensor 402 may sense a body part of a user and generate a command. The sensor 402 may include one or more devices that may respond to a first physical phenomenon (e.g., electromagnetic waves ("light"), vibration, temperature differences, etc.) or a plurality of physical phenomena. The sensor 402 may detect light in a frequency range. The frequency range may be one of radio waves, microwaves, infrared, near-infrared, visible light, ultraviolet, and/or x-rays, or a combination thereof. Suppose that a user places a hand within the sensory range of the sensor 402. By monitoring for a change in reflected light, the sensor 402 may detect the presence of a hand or the motion thereof and may generate a command to activate the modular fluid dispensing system 400 in response.

As discussed previously, the dispenser lower section 312 includes a nozzle 404. The nozzle 404 may be located at the top of the dispenser lower section 312 under the dispenser upper section 300. The nozzle 404 includes a first opening (not shown) such that the fluid to be dispensed may flow out of the first opening. The tubing system 306 provides a fluid connection between the fluid port 302, the pump 304, and the nozzle 404. The size and cross-section of the nozzle 404 may achieve desirable flow characteristics in the fluid being dispensed.

Suppose a user also wishes to adjust the volume of the fluid being dispensed. The user may adjust the volume of the fluid being dispensed by moving a selector switch (not shown). The command received by the pump 304 instructs the pump 304 to dispense the fluid in response to a selection of a position of the selector switch. The volume of fluid dispensed may be varied by adjusting the time duration of the command received by the pump 304. The modular fluid dispensing system 100 may include a means for the user to initiate and halt the command received by the pump 304 such that the user may control the volume dispensed. In an implementation, the selector switch is located on an exterior surface of the modular fluid dispensing system 100. In another implementation, the selector switch is located on an interior surface of the dispenser lower section 312 and the removable face plate 110 may at least partially cover the selector switch (not shown), such that in response to removing the removable face plate 110 the selector switch is at least partially uncovered.

To determine the volume of fluid being dispensed, a control unit (not shown) may incorporate signals from one or more sources. A first sensor (not shown) may detect electrical current flowing through a motor of the pump 304 and provide a first signal such that the number of pump rotations may be determined. A second sensor (not shown) is located in the flow path of the fluid and rotates in response to the flow of the fluid through the tubing system 306 to provide a second signal such that the volumetric flowrate of the fluid may be determined directly. Either or both of the first signal and the second signal may be used to determine the fill status of the bottle (not shown) as described in greater detail in the following paragraphs. The second sensor may detect movement of the fluid. The second sensor may also detect electrical current flowing through a motor of the pump.

Figure 5:
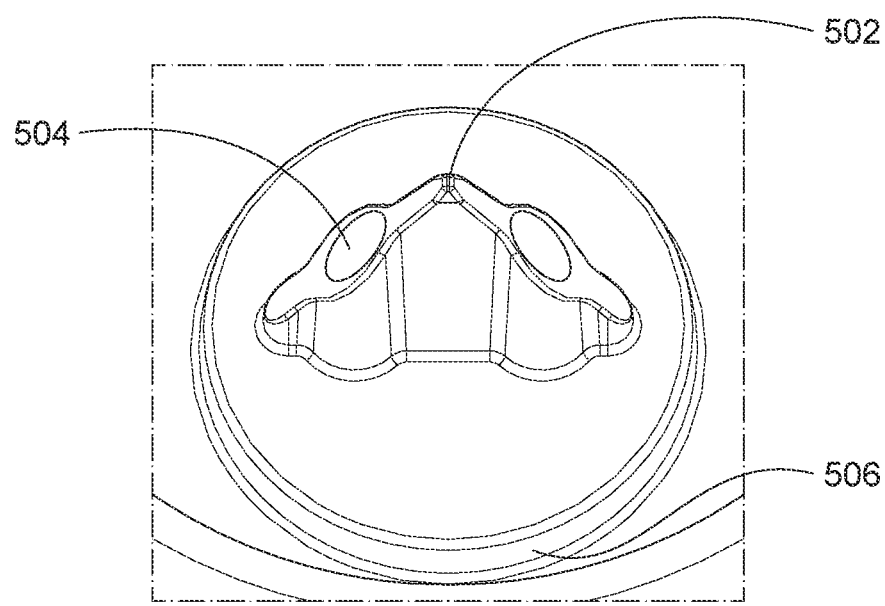
FIG. 5 illustratively depicts an internal view of a bottle housing, in accordance with an implementation of the disclosure.

FIG. 5 illustratively depicts an internal view of a bottle housing 500. The bottle housing 500 includes a puncturing taper 502, a fluid port 504, and a threaded fastener 506. The threaded fastener 506 is affixed to the bottom of the bottle housing 500. The puncturing taper 502 and fluid port 504 are affixed to the threaded fastener 506. The puncturing taper 502 may be the same as the puncturing taper 202 as described in FIG. 2 above. The fluid port 504 may be the same as the fluid port 206 or the fluid port 302 as described in FIGS. 2 and 3A above, respectively. The threaded fastener 506 may be the same as the threaded faster 204 as described in FIG. 2 above.

As described above, the bottle housing 500 may encircle and at least partially enclose a bottle (not shown). The threaded fastener 506 includes one of a first male connection or a first female connection which may couple to one of a second male or a second female connection of the bottle at a thread angle. In an implementation, the thread angle ranges between 2 and 12 degrees. In another implementation, the thread angle is greater than 12 degrees. The threaded fastener is configured such that in response to rotation of a bottle a fluid seal is formed between the threaded fastener 506 and the bottle as will be described below.

Now, suppose that a user wishes to attempt to pilfer the bottle from a modular fluid dispensing system 100. A potential method of reducing loss due to theft is to frustrate the perpetrator with unexpected results. The removable lid 102 may be configured such that the removable lid 102 couples to the bottle housing 105 in response to a counter-clockwise rotation of the removable lid 102 ("reverse threads"). Alternatively, the bottle (not shown) may be configured such that the fluid seal is formed in response to a counter-clockwise rotation of the bottle. The use of reverse threads may confuse and/or frustrate a user without knowledge of the design and operation of the modular fluid dispensing system 100 and so prevent a theft.

Shipping and handling of bottles containing a volume of fluid introduces a potential for leakage. Thus, bottles for use with the modular fluid dispensing system 100 may include a seal. The bottle (not shown) includes a membrane seal over the mouth of the bottle to prevent leakage during shipping and handling. The bottle housing 500 includes a puncturing taper 502 which may puncture a membrane seal of the bottle during installation of the bottle and thus initiate flow of the fluid contained therein. The puncturing taper 502 may be constructed from any one of a metal, a glass, a plastic, or a combination thereof.

Following the puncturing of the membrane seal by the puncturing taper 502, the fluid contained inside the bottle comes into contact with the fluid port 504. The fluid port 504 includes a first opening of a first flow channel and a first opening of a second flow channel. The first flow channel and second flow channel provide a fluid connection between the bottle housing 500 and the components included in the dispenser upper section 300 as described above.

The first flow channel is in fluid connection with the pump 304 and the second flow channel is in fluid connection with the vacuum break port 310. As described previously, the vacuum break port 310 may permit ingress of another fluid, such as air, into the bottle (not shown) such that the removal of the fluid contained inside the bottle by the pump 304 prevents a vacuum from forming in the bottle. Alternatively, the vacuum break port 310 may admit a fluid to pressurize the bottle through the fluid port 504.

Figure 6:
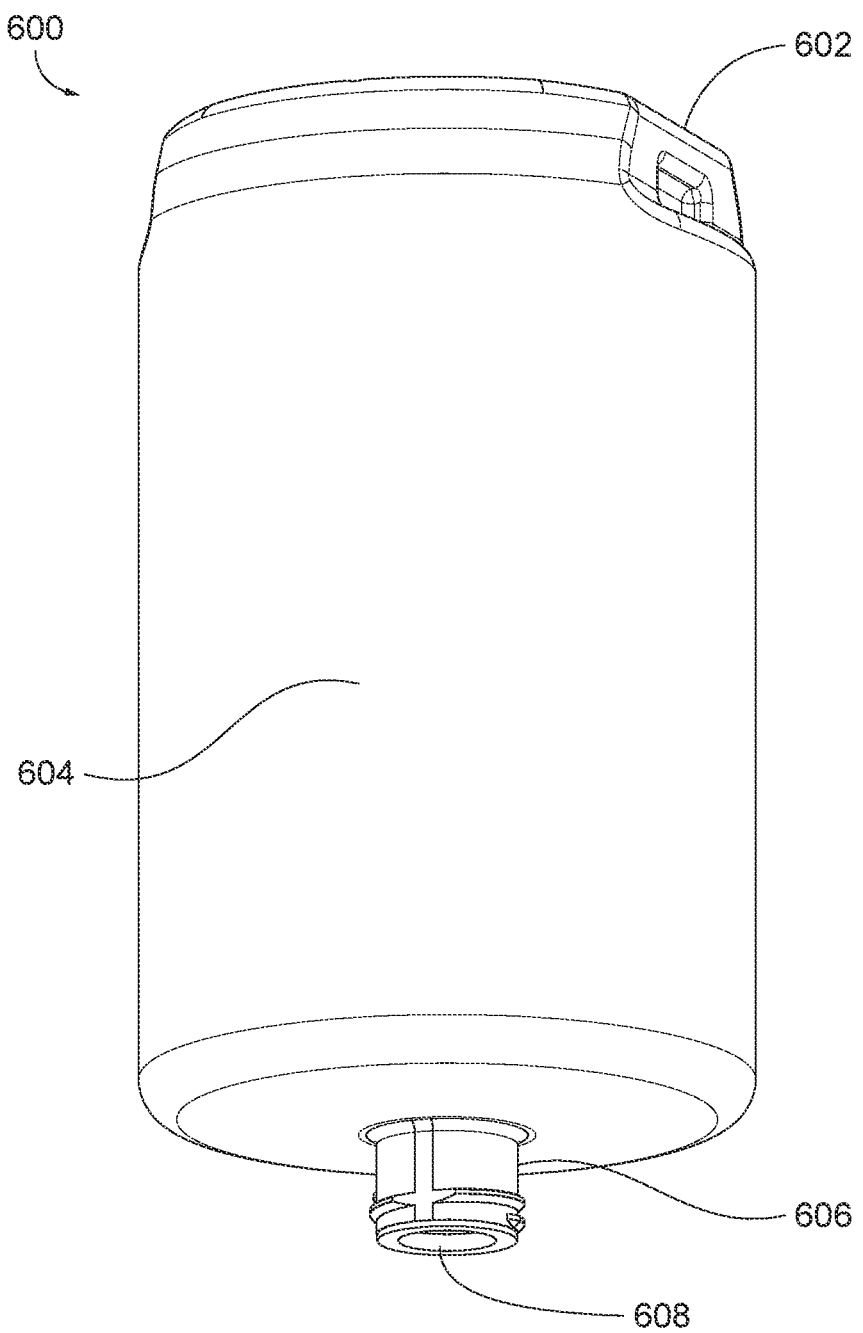
FIG. 6 illustratively depicts a bottle, in accordance with an implementation of the disclosure.

FIG. 6 illustratively depicts a bottle 600. The bottle 600 includes a concave surface 602, a bottle body 604, a bottle threaded fastener 606, and a mouth 608. In an implementation, the bottle 600 may be encircled and may at least be partially enclosed by the bottle housing 500 as described above. In another implementation, the bottle is configured to be housed separately from the modular fluid dispensing system 100.

The bottle 600 is a vessel for retaining and transporting a fluid to be dispensed from the modular fluid dispensing system 100. The bottle 600 may be constructed from any material suitable for the fluid contained within and the rigors of transportation, including a plastic, a glass, a metal, or a combination thereof. The bottle 600 includes a concave surface 602 which may enable a user to grip the bottle 600 with a finger.

Suppose that there is a minimal gap between the bottle body 604 and the bottle housing shell 208. Using the concave surface 602, a user may grip the bottle 600 from the top with one or more fingers to form the fluid seal. This configuration provides the user with an affordance for ease of installation and removal of the bottle 600.

The bottle 600 includes a mouth 608 which may allow filling and emptying of the bottle 600. The mouth 608 is sealed with a membrane seal after the bottle is filling with the fluid to be dispensed such that leakage during shipping and handling is minimized. The membrane seal includes one or more layers of foil, plastic, paper, waxed paper, or a combination thereof. During installation, the membrane seal may be punctured by a puncturing taper 502 to initiate flow of the fluid from the bottle as described above.

Installation of a bottle 600 into the modular fluid dispensing system 100 may require removal of the removable lid 102 and rotating the bottle 600 such that a fluid seal is formed between the threaded fastener 506 and the bottle threaded fastener 606. The bottle threaded fastener 606 includes one of a first male connection or a first female connection which may couple to one of a second male or a second female connection of the threaded fastener 506 at a thread angle. In an implementation, the thread angle ranges between 2 and 12 degrees. In another implementation, the thread angle is greater than 12 degrees. Following installation of the bottle 600, the removable lid 102 may be reinstalled.

Figure 7A:
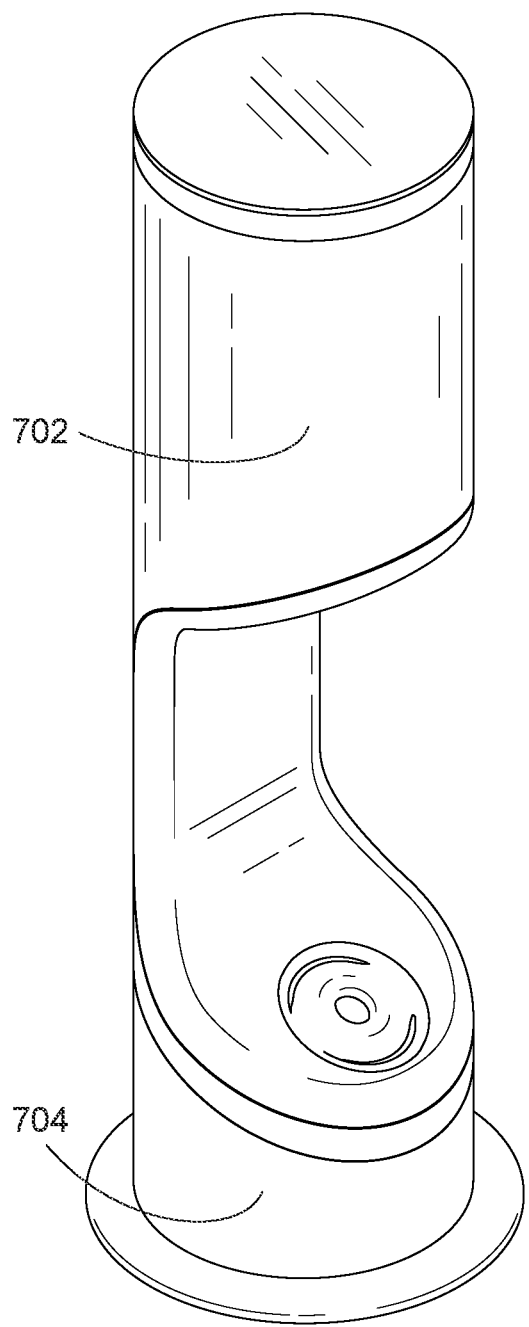
FIG. 7A illustratively depicts a modular fluid dispensing system with a desk base unit, in accordance with an implementation of the disclosure.

FIG. 7A illustratively depicts a modular fluid dispensing system with a desk base unit 700. The modular fluid dispensing system with a desk base unit 700 includes a modular fluid dispensing system 702 and a desk base unit 704. The modular fluid dispensing system 702 may be the same as the modular fluid dispensing system 100 or the modular fluid dispensing system 400 as described in FIGS. 1 and 4 above, respectively.

The modular nature of the attachment mechanism (not shown) provides users the flexibility to toggle the modular fluid dispensing system 100 between various forms. In an implementation, the attachment mechanism may couple the body to a support structure to support the modular fluid dispensing system 702, such as a wall. In another implementation, however, the attachment mechanism may couple the body to either or both of a support structure or at least one of a plurality of base units that can support the modular fluid dispensing system.

The desk base unit 704 is located under the modular fluid dispensing system 702 and may be removably affixed by the attachment mechanism (not shown). One or more positioning posts (not shown) and one or more captive screw assemblies (not shown) may be included in the attachment mechanism as described above. Suppose a user wishes to place one or more modular fluid dispensing systems 702 on tables and/or desks. The desk base unit 704 supports the modular fluid dispensing system 702 on a flat surface such as a table and provides a comfortable height for a user to access. Alternatively, a user may choose to deploy one or more modular fluid dispensing systems 702 on floors using the floor base unit described below.

Figure 7B:
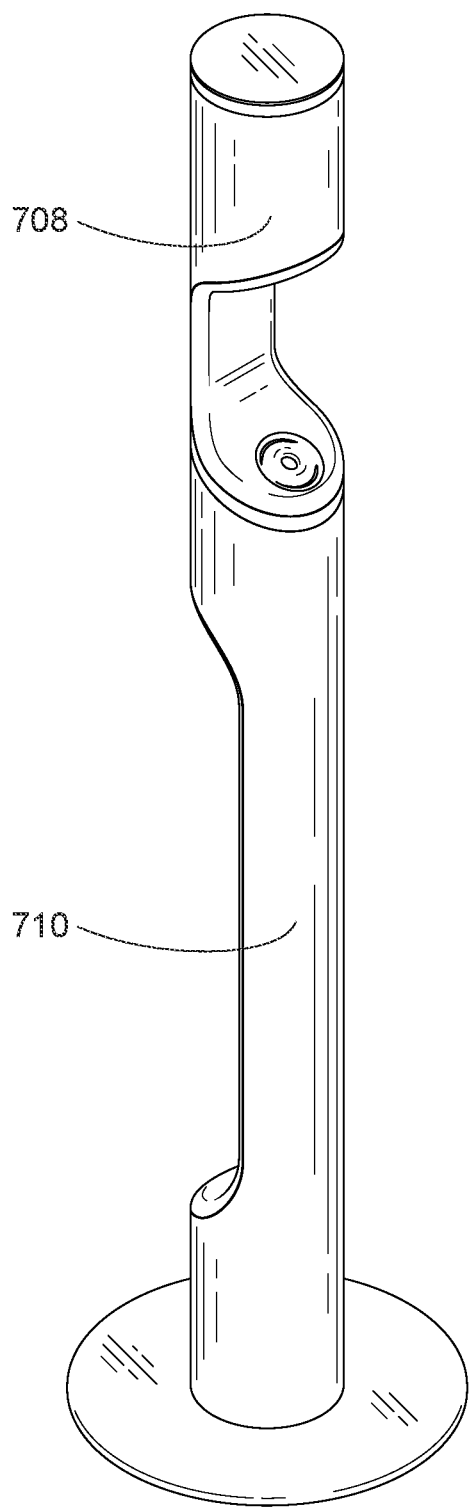
FIG. 7B illustratively depicts a modular fluid dispensing system with a floor base unit, in accordance with an implementation of the disclosure.

FIG. 7B illustratively depicts a modular fluid dispensing system with a floor base unit 706. The modular fluid dispensing system with a floor base unit 706 includes a modular fluid dispensing system 708 and a floor base unit 710. The modular fluid dispensing system 708 may be the same as the modular fluid dispensing system 100, the modular fluid dispensing system 400, or the modular fluid dispensing system 702 as described in FIGS. 1, 4, and 7A above, respectively.

The floor base unit 710 is located under the modular fluid dispensing system 708 and may be removably affixed by the attachment mechanism (not shown). One or more positioning posts (not shown) and one or more captive screw assemblies (not shown) may be included in the attachment mechanism as described above. The floor base unit 710 supports the modular fluid dispensing system 708 on a flat surface such as a floor and provides a comfortable height for better user access. In addition, the floor base unit 710 may include one or more LEDs for safety lighting.

Figure 8A:
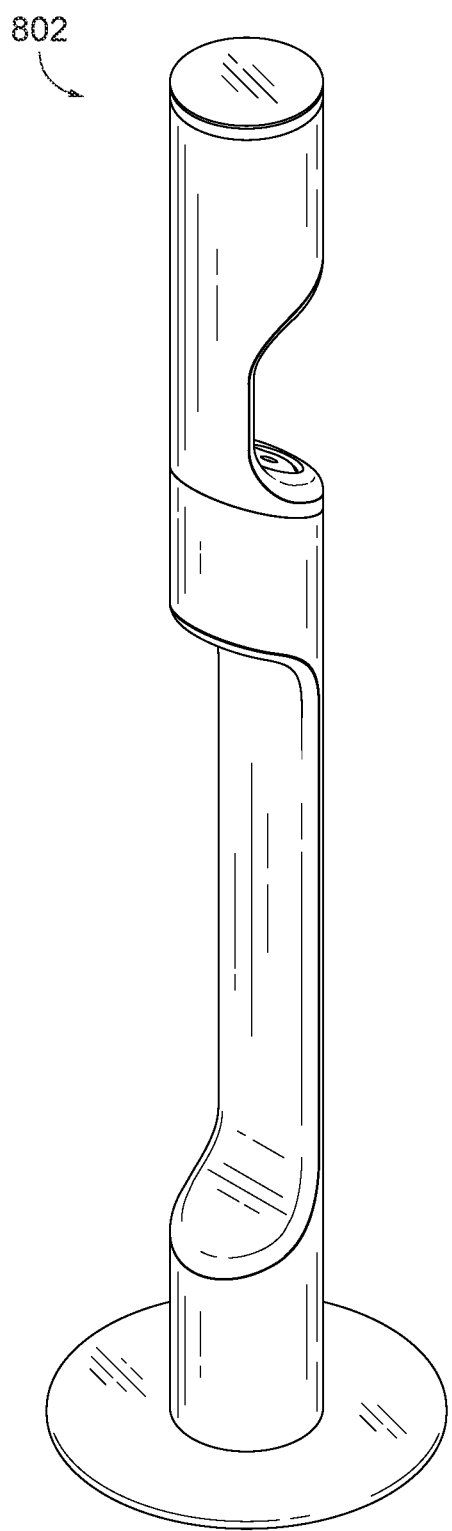
FIG. 8A illustratively depicts the rear isometric view of a modular fluid dispensing system with a floor base unit, in accordance with an implementation of the disclosure.

FIG. 8A illustratively depicts the rear isometric view of a modular fluid dispensing system with a floor base unit 802.

Figure 8B:
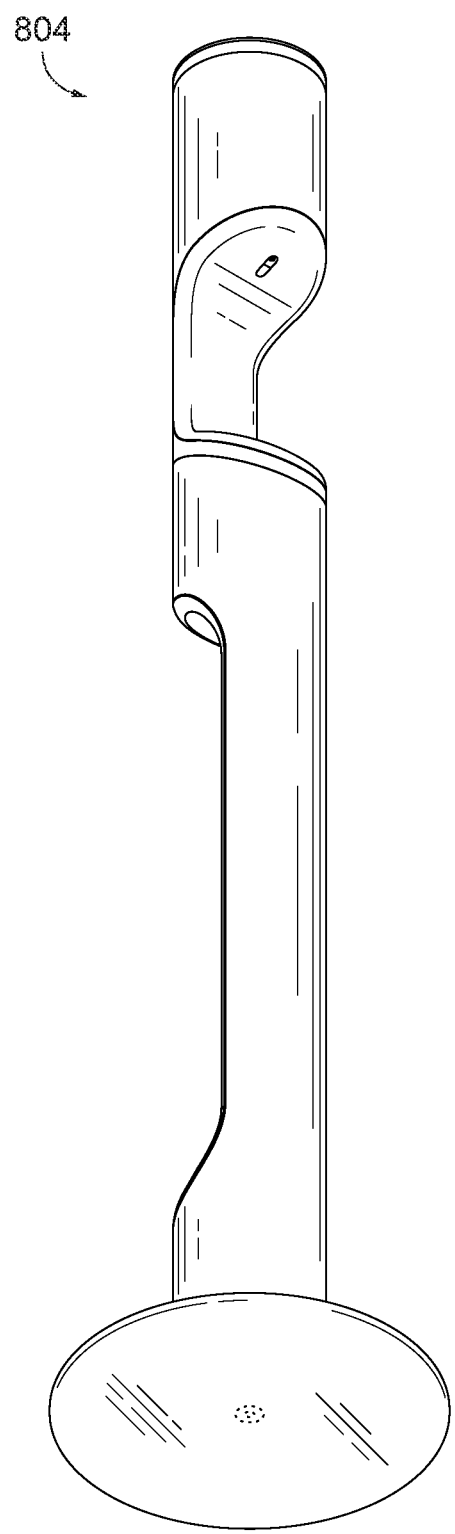
FIG. 8B illustratively depicts the front isometric view of a modular fluid dispensing system with a floor base unit, in accordance with an implementation of the disclosure.

FIG. 8B illustratively depicts the front isometric view of a modular fluid dispensing system with a floor base unit 804.

Figure 8C:
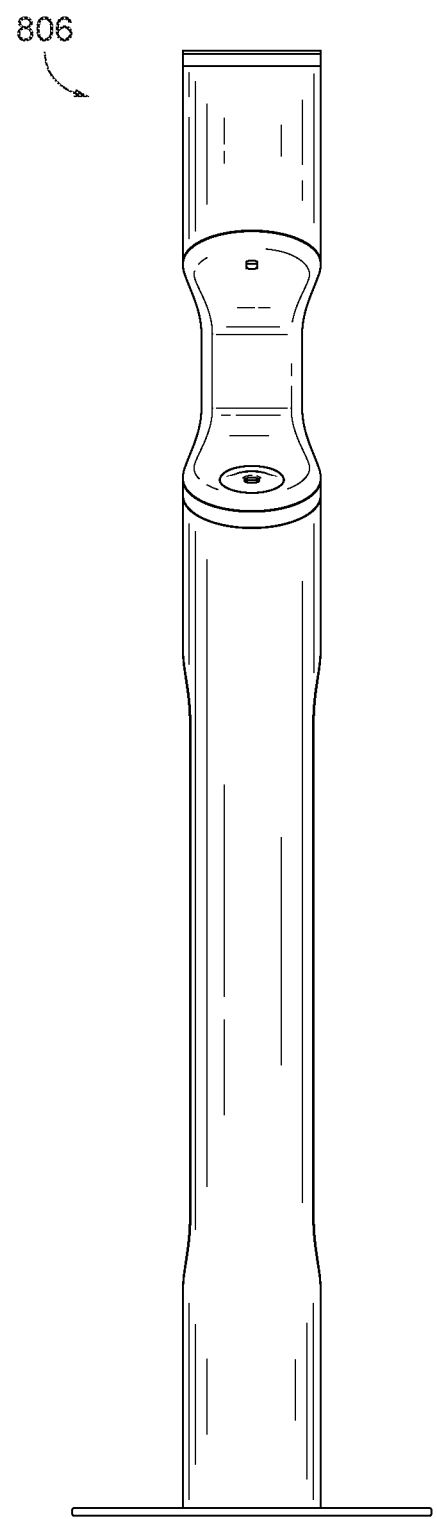
FIG. 8C illustratively depicts the front view of a modular fluid dispensing system with a floor base unit, in accordance with an implementation of the disclosure.

FIG. 8C illustratively depicts the front view of a modular fluid dispensing system with a floor base unit 806.

Figure 8D:
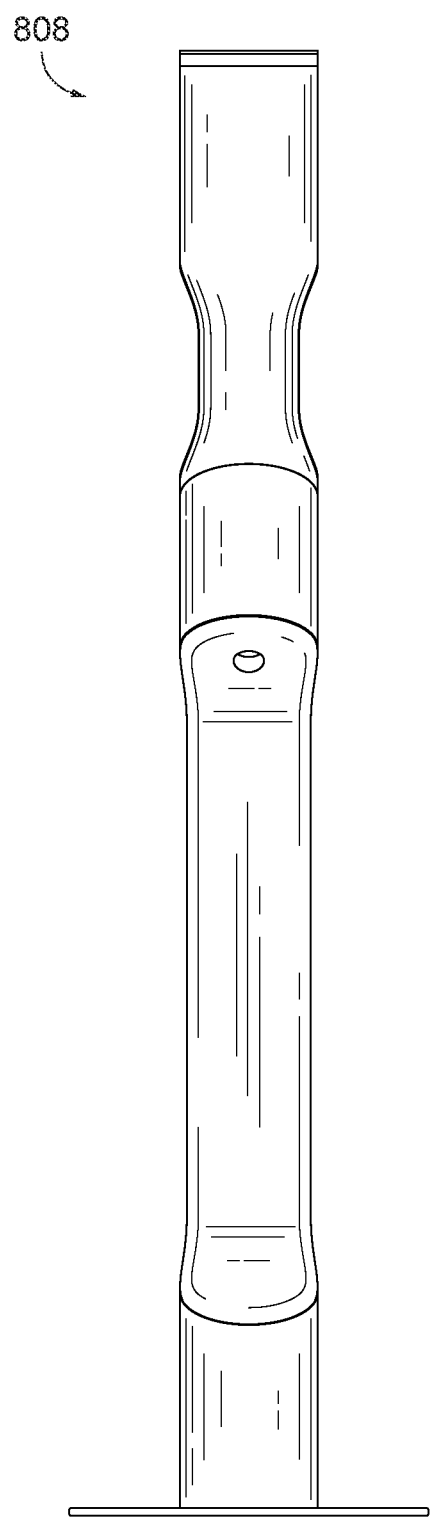
FIG. 8D illustratively depicts the back view of a modular fluid dispensing system with a floor base unit, in accordance with an implementation of the disclosure.

FIG. 8D illustratively depicts the back view of a modular fluid dispensing system with a floor base unit 808.

Figure 8E:
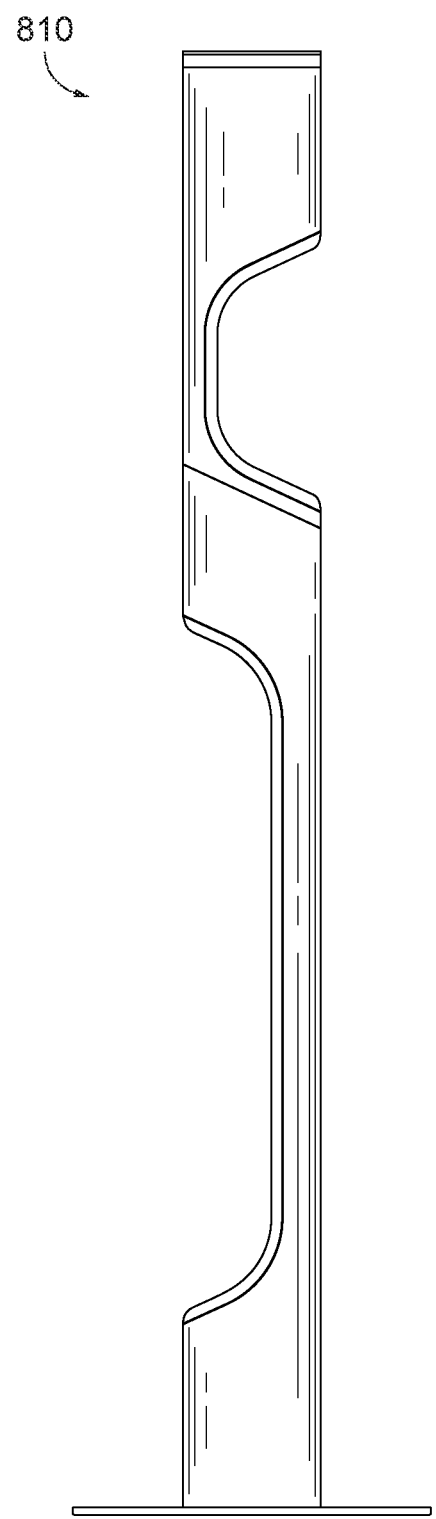
FIG. 8E illustratively depicts the left view of a modular fluid dispensing system with a floor base unit, in accordance with an implementation of the disclosure.

FIG. 8E illustratively depicts the left view of a modular fluid dispensing system with a floor base unit 810.

Figure 8F:
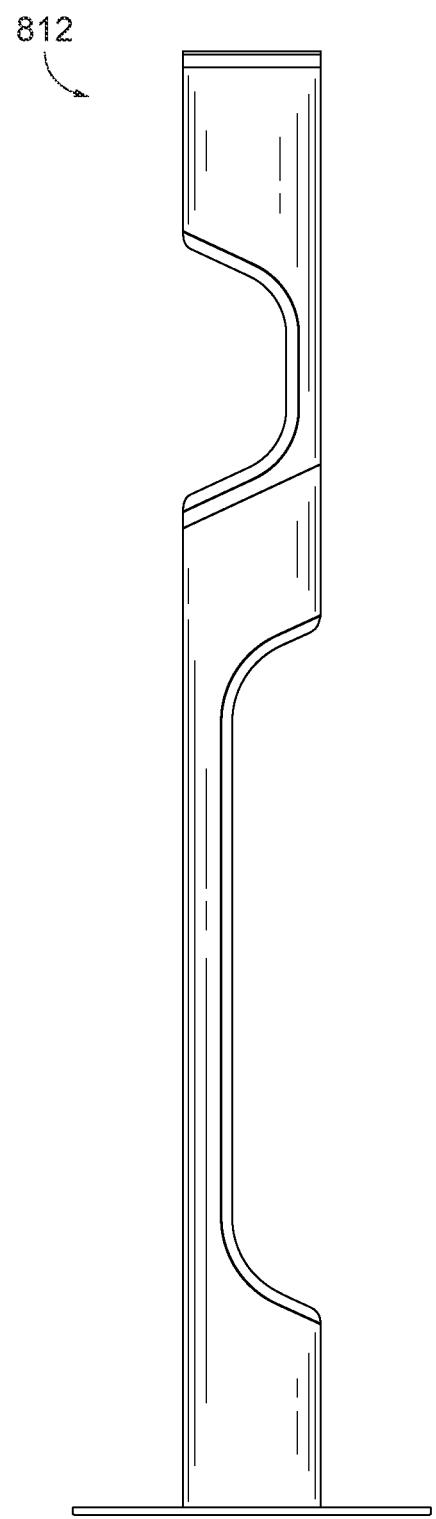
FIG. 8F illustratively depicts the right view of a modular fluid dispensing system with a floor base unit, in accordance with an implementation of the disclosure.

FIG. 8F illustratively depicts the right view of a modular fluid dispensing system with a floor base unit 812.

Figure 8G:
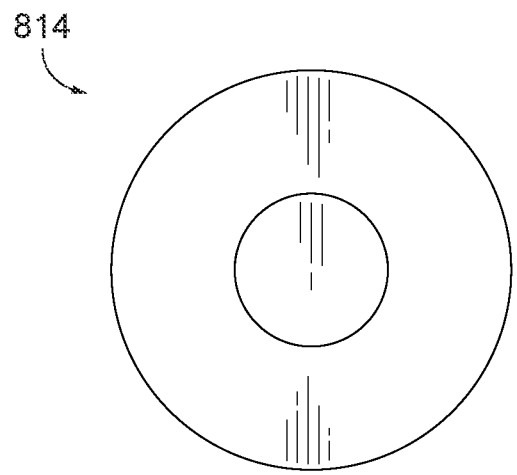
FIG. 8G illustratively depicts the top view of a modular fluid dispensing system with a floor base unit, in accordance with an implementation of the disclosure.

FIG. 8G illustratively depicts the top view of a modular fluid dispensing system with a floor base unit 814.

Figure 8H:
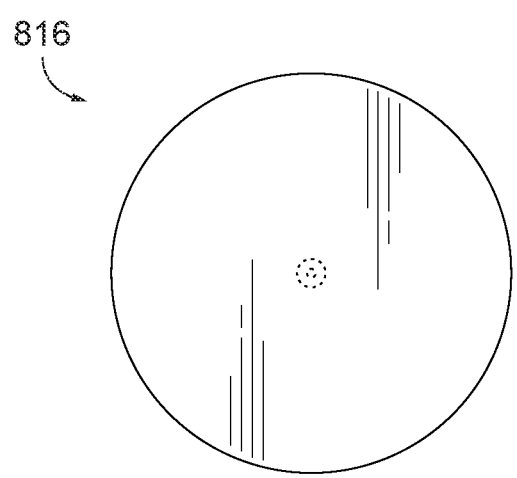
FIG. 8H illustratively depicts the bottom view of a modular fluid dispensing system with a floor base unit, in accordance with an implementation of the disclosure.

FIG. 8H illustratively depicts the bottom view of a modular fluid dispensing system with a floor base unit 816.

Figure 8I:
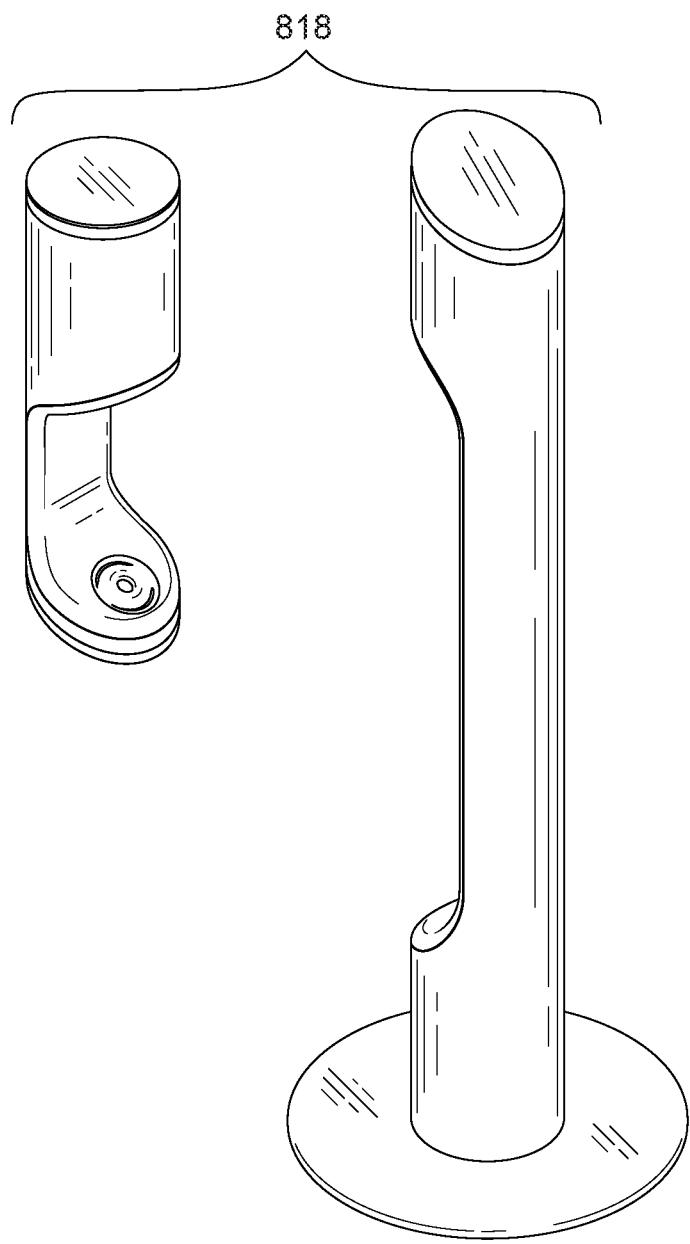
FIG. 8I illustratively depicts an exploded isometric view of a modular fluid dispensing system with a floor base unit, in accordance with an implementation of the disclosure.

FIG. 8I illustratively depicts an exploded isometric view of a modular fluid dispensing system with a floor base unit 818.

The description of the modular fluid dispensing system with a floor base unit 706 in FIG. 7B applies to FIGS. 8A-8I.

Figure 9A:
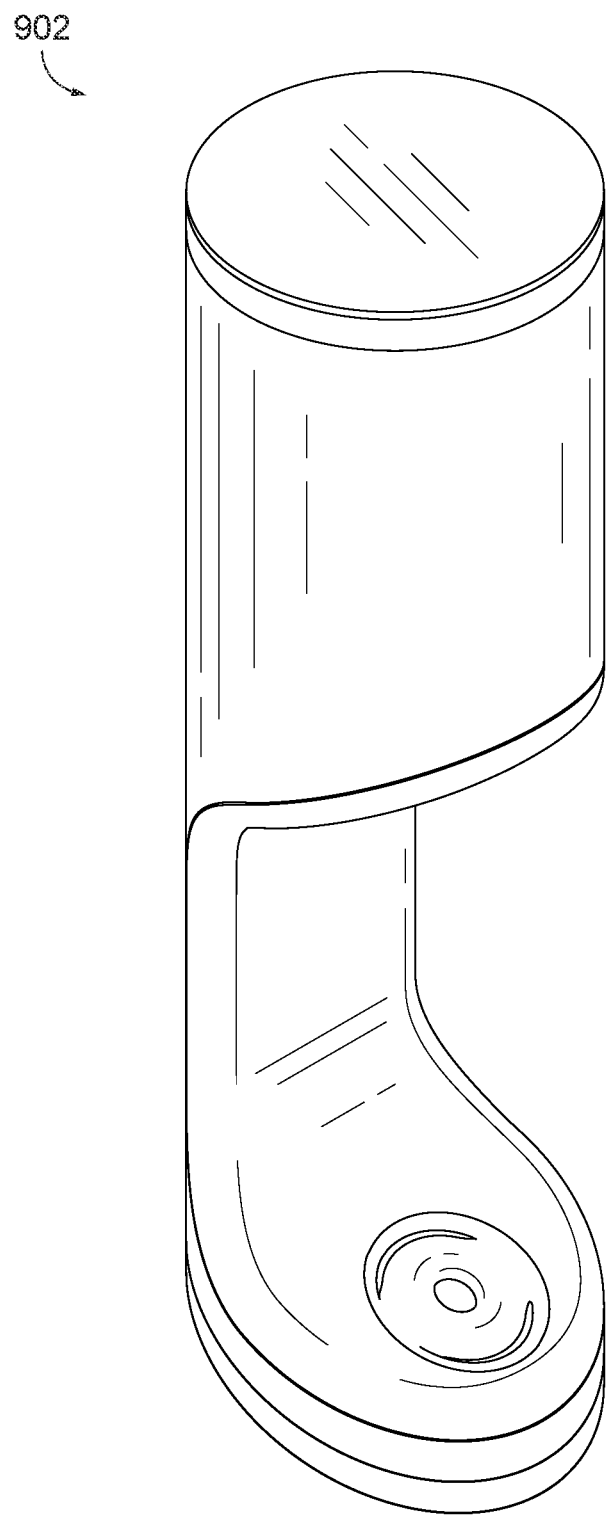
FIG. 9A illustratively depicts the upper front isometric view of a modular fluid dispensing system, in accordance with an implementation of the disclosure.

FIG. 9A illustratively depicts the upper front isometric view of a modular fluid dispensing system 902.

Figure 9B:
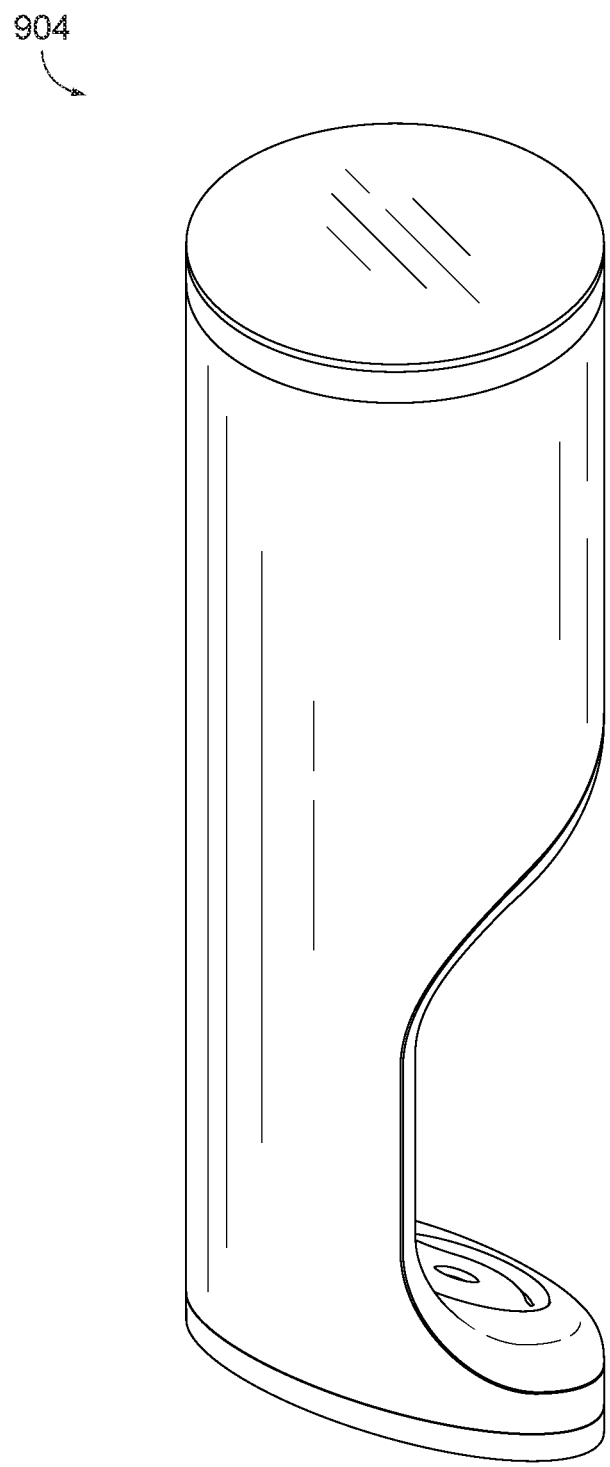
FIG. 9B illustratively depicts the back isometric view of a modular fluid dispensing system, in accordance with an implementation of the disclosure.

FIG. 9B illustratively depicts the back isometric view of a modular fluid dispensing system 904.

Figure 9C:
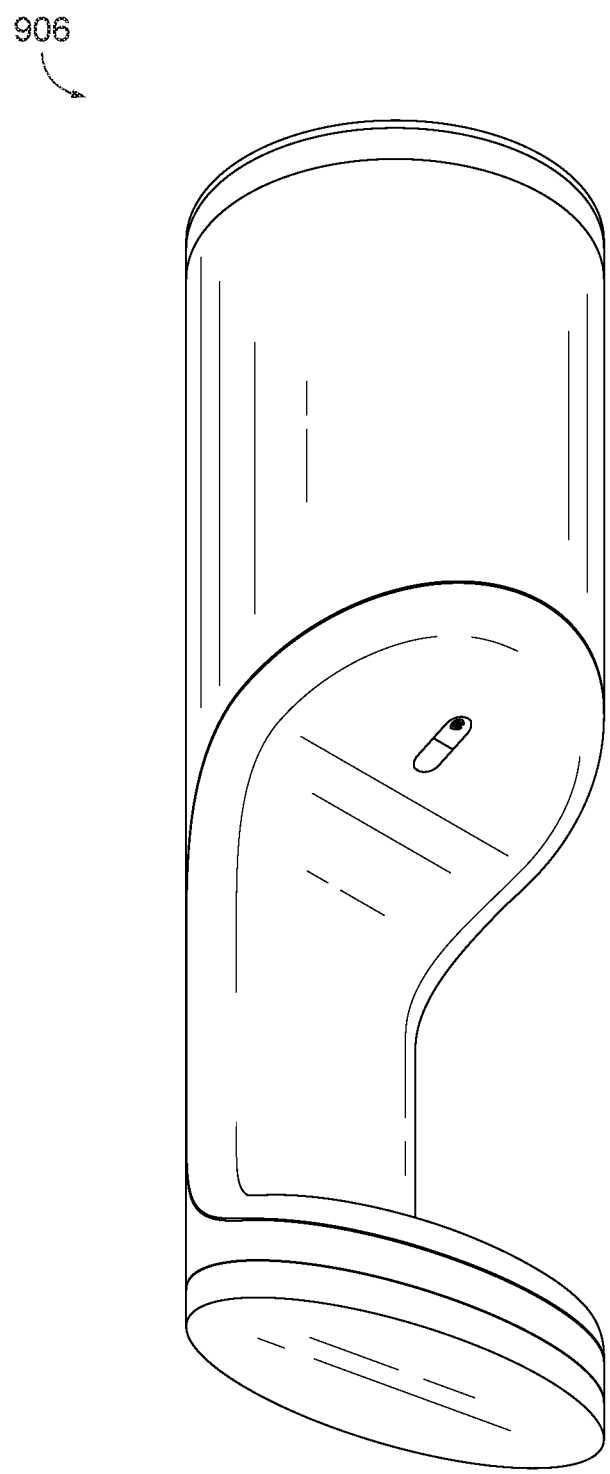
FIG. 9C illustratively depicts the lower front isometric view of a modular fluid dispensing system, in accordance with an implementation of the disclosure.

FIG. 9C illustratively depicts the lower front isometric view of a modular fluid dispensing system 906.

Figure 9D:
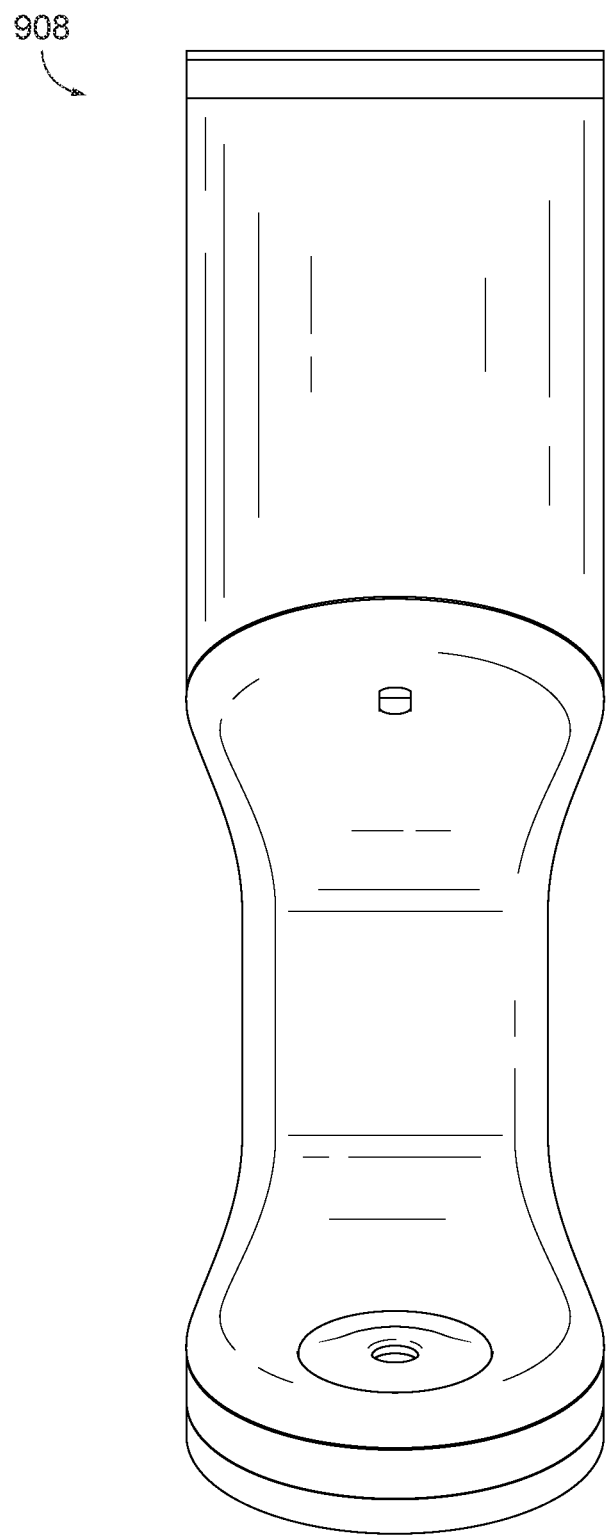
FIG. 9D illustratively depicts the front view of a modular fluid dispensing system, in accordance with an implementation of the disclosure.

FIG. 9D illustratively depicts the front view of a modular fluid dispensing system 908.

Figure 9E:
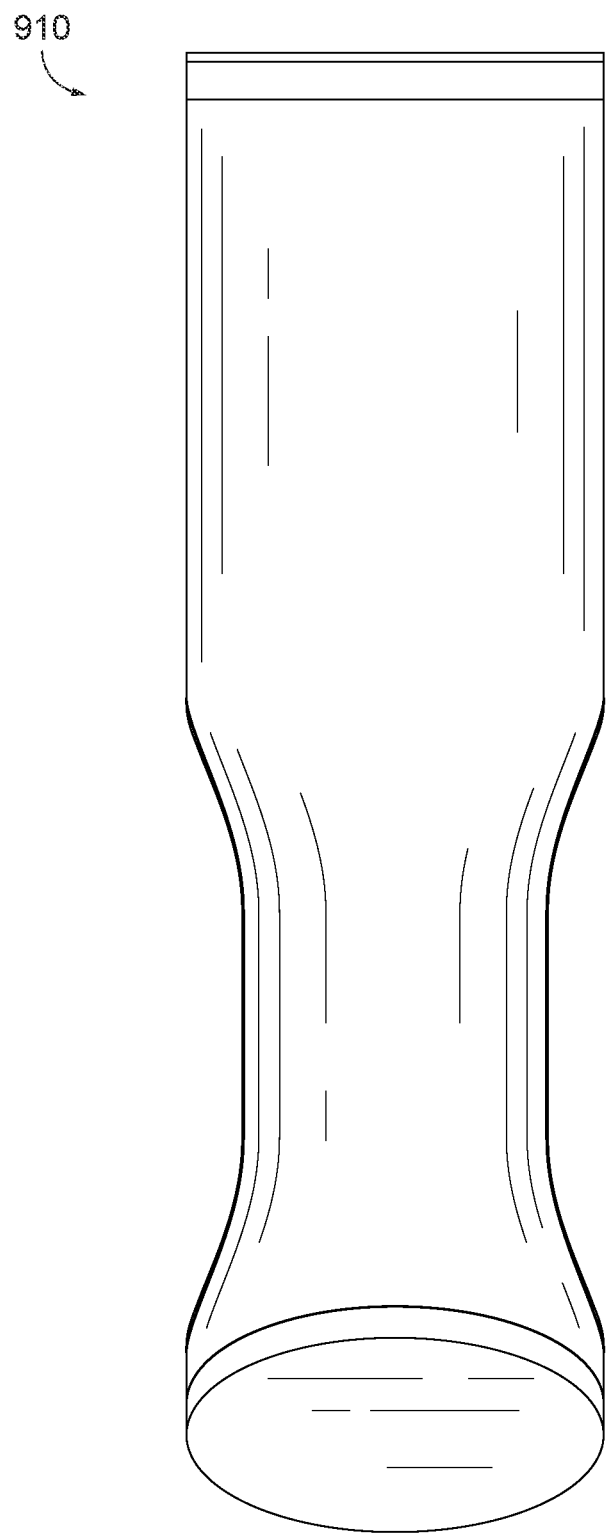
FIG. 9E illustratively depicts the back view of a modular fluid dispensing system, in accordance with an implementation of the disclosure.

FIG. 9E illustratively depicts the back view of a modular fluid dispensing system 910.

Figure 9F:
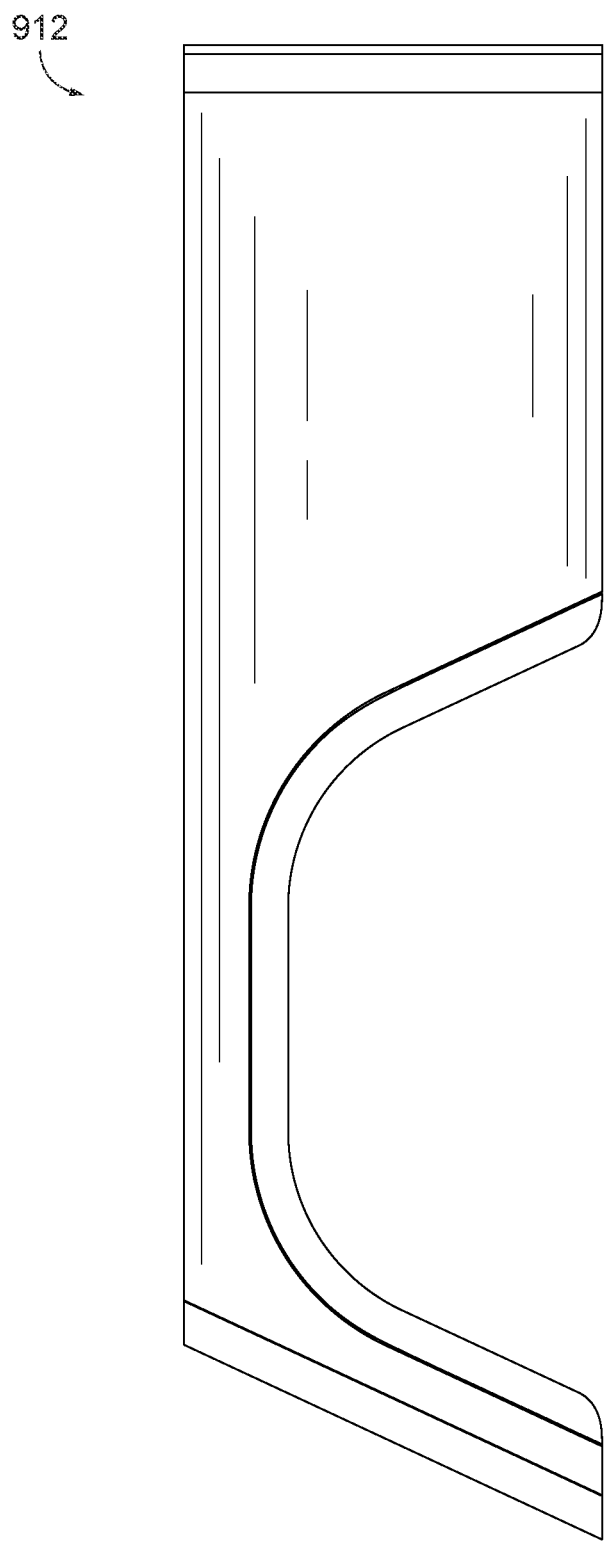
FIG. 9F illustratively depicts the left view of a modular fluid dispensing system, in accordance with an implementation of the disclosure.

FIG. 9F illustratively depicts the left view of a modular fluid dispensing system 912.

Figure 9G:
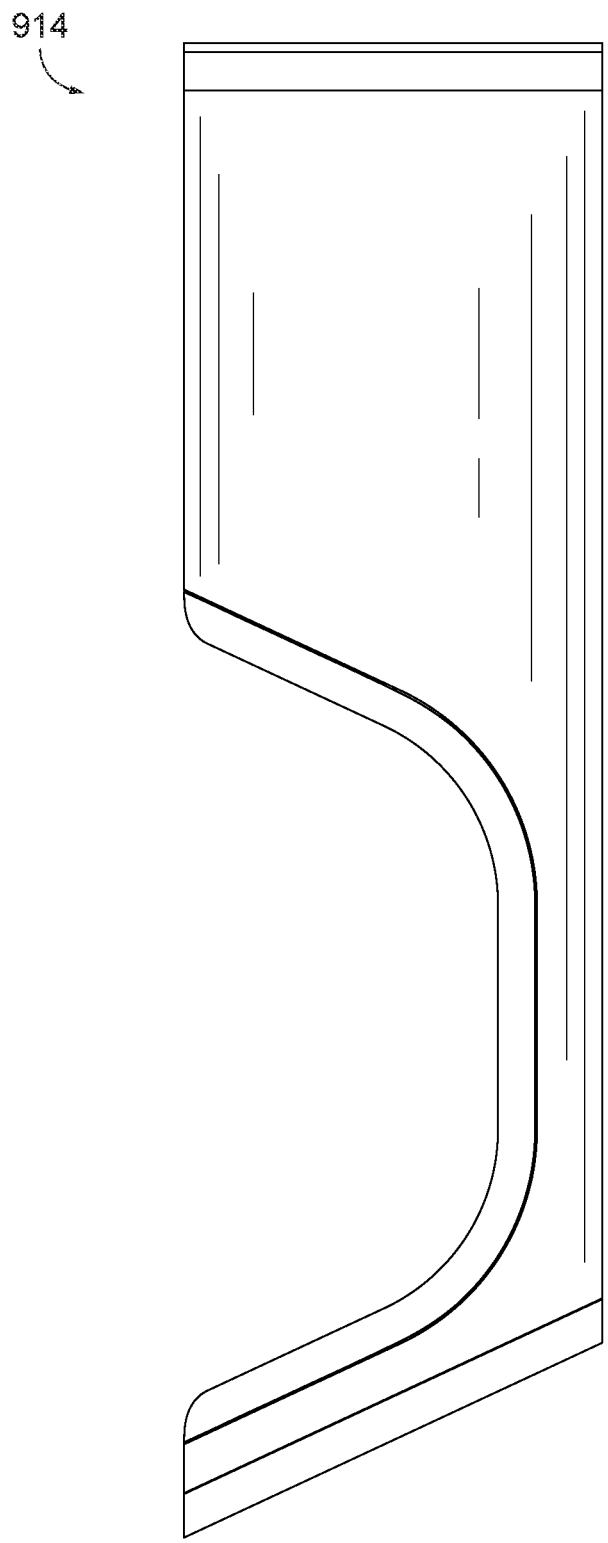
FIG. 9G illustratively depicts the right view of a modular fluid dispensing system, in accordance with an implementation of the disclosure.

FIG. 9G illustratively depicts the right view of a modular fluid dispensing system 914.

Figure 9H:
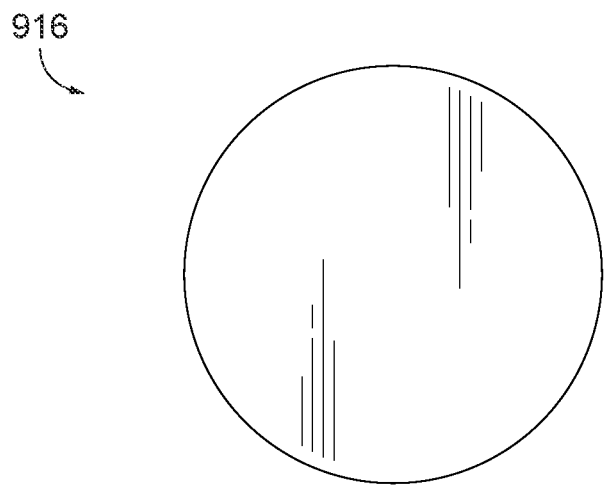
FIG. 9H illustratively depicts the top view of a modular fluid dispensing system, in accordance with an implementation of the disclosure.

FIG. 9H illustratively depicts the top view of a modular fluid dispensing system 916.

Figure 9I:
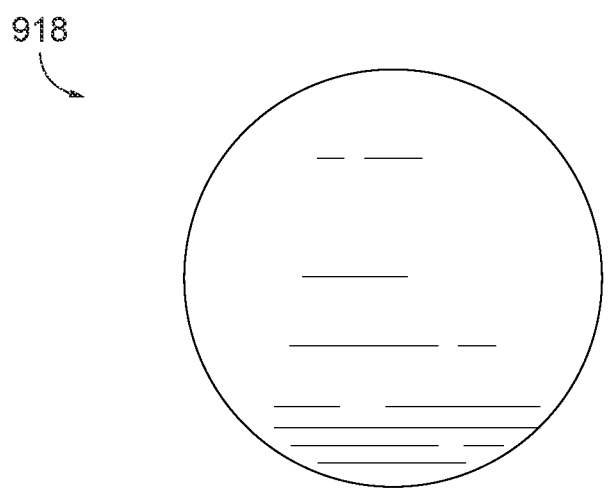
FIG. 9I illustratively depicts the bottom view of a modular fluid dispensing system, in accordance with an implementation of the disclosure.

FIG. 9I illustratively depicts the bottom view of a modular fluid dispensing system 918.

The description of the modular fluid dispensing system 100 in FIG. 1 applies to FIGS. 9A-9I.

Figure 10A:
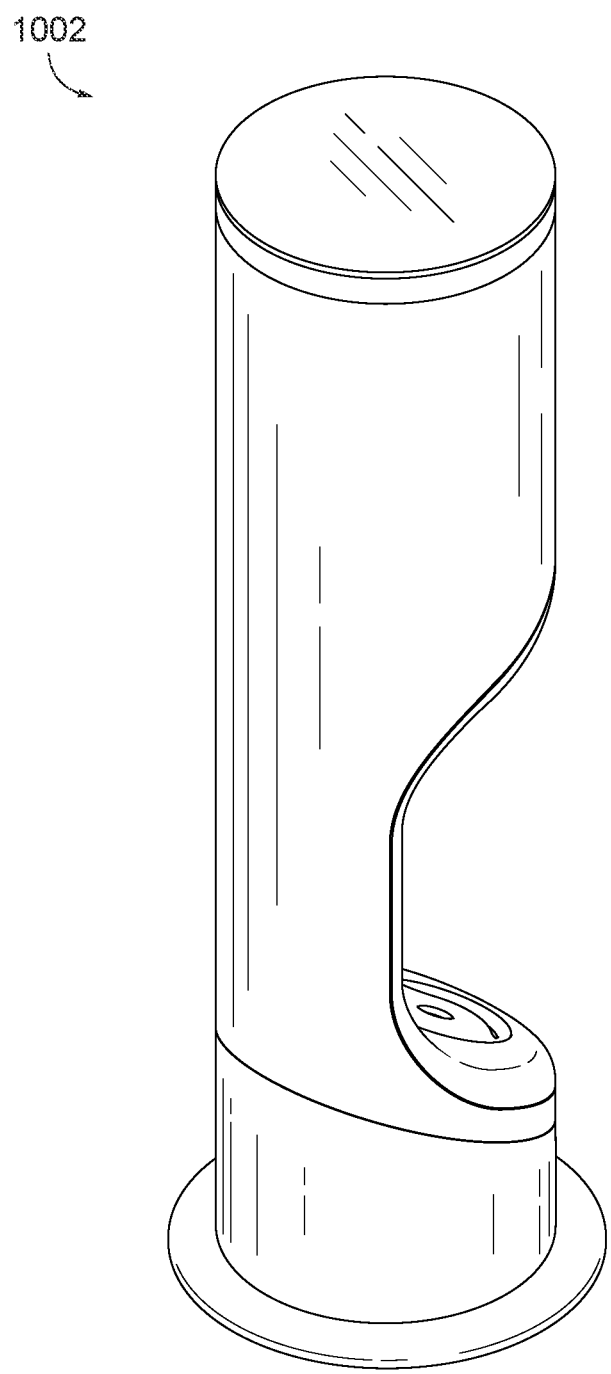
FIG. 10A illustratively depicts the rear isometric view of a modular fluid dispensing system with a floor base unit, in accordance with an implementation of the disclosure.

FIG. 10A illustratively depicts the rear isometric view of a modular fluid dispensing system with a floor base unit 1002.

Figure 10B:
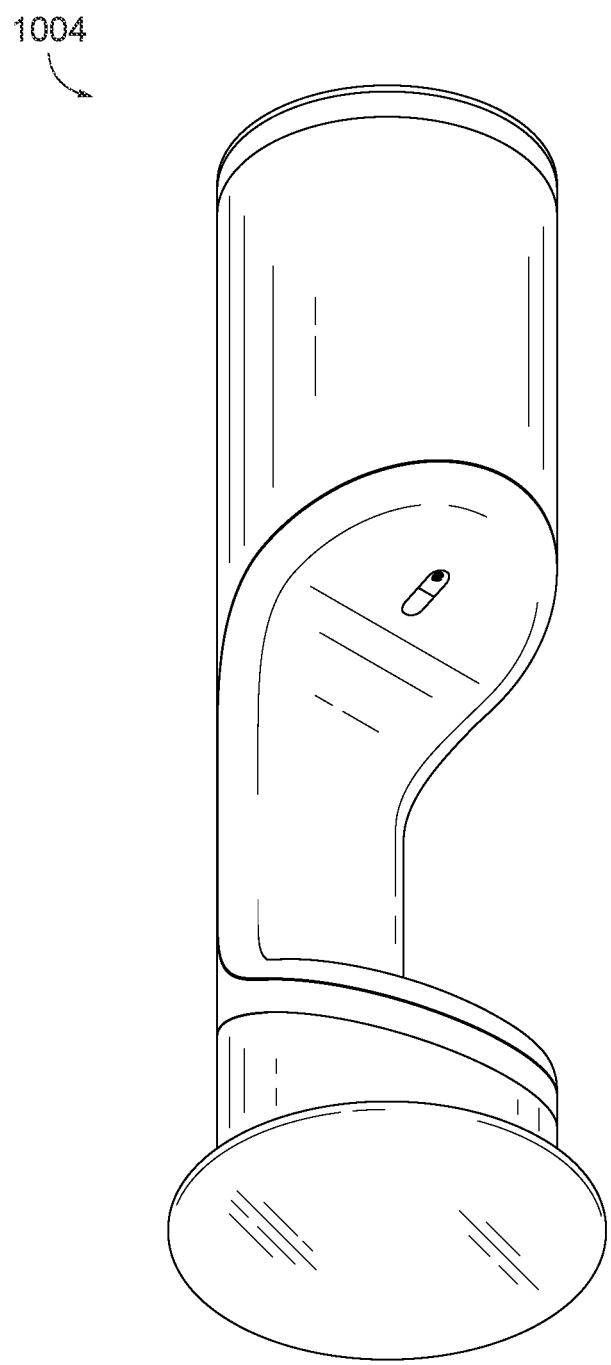
FIG. 10B illustratively depicts the front isometric view of a modular fluid dispensing system with a floor base unit, in accordance with an implementation of the disclosure.

FIG. 10B illustratively depicts the front isometric view of a modular fluid dispensing system with a floor base unit 1004.

Figure 10C:
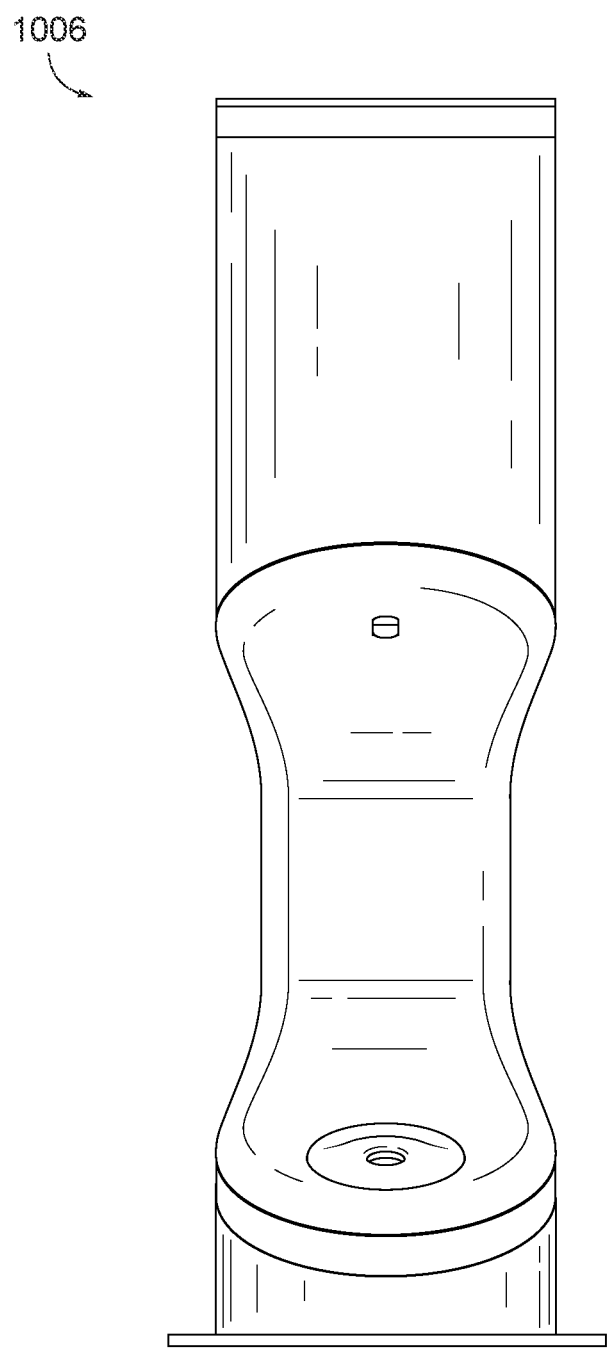
FIG. 10C illustratively depicts the front view of a modular fluid dispensing system with a floor base unit, in accordance with an implementation of the disclosure.

FIG. 10C illustratively depicts the front view of a modular fluid dispensing system with a floor base unit 1006.

Figure 10D:
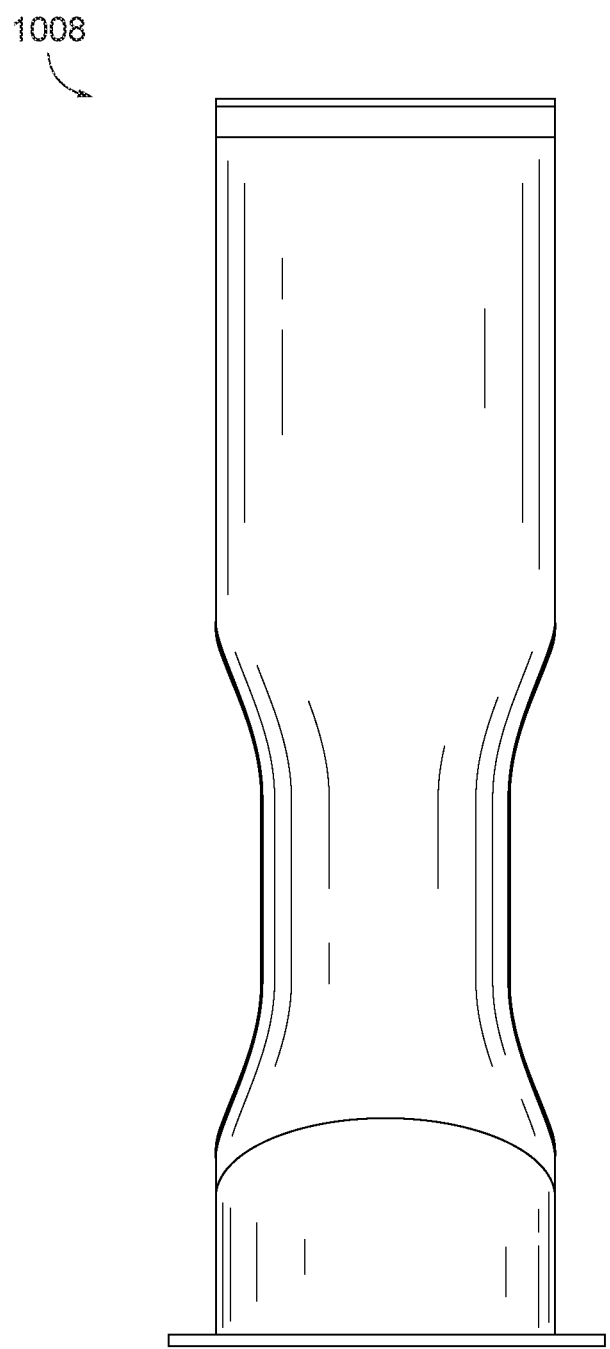
FIG. 10D illustratively depicts the back view of a modular fluid dispensing system with a floor base unit, in accordance with an implementation of the disclosure.

FIG. 10D illustratively depicts the back view of a modular fluid dispensing system with a floor base unit 1008.

Figure 10E:
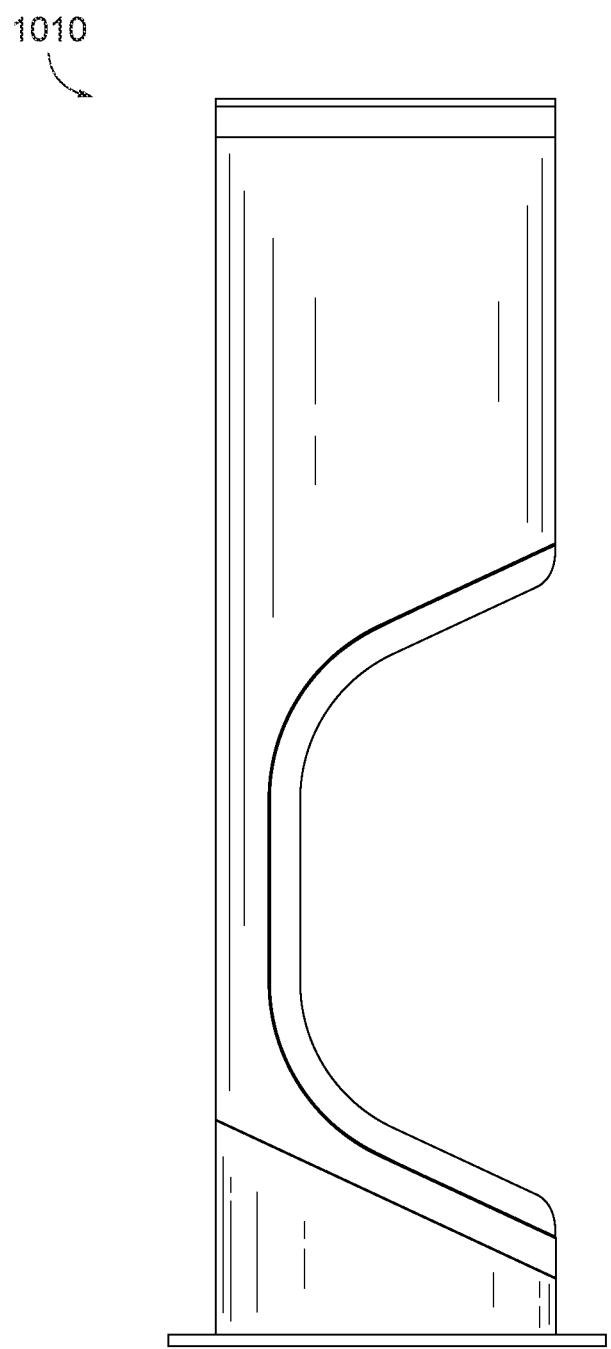
FIG. 10E illustratively depicts the left view of a modular fluid dispensing system with a floor base unit, in accordance with an implementation of the disclosure.

FIG. 10E illustratively depicts the left view of a modular fluid dispensing system with a floor base unit 1010.

Figure 10F:
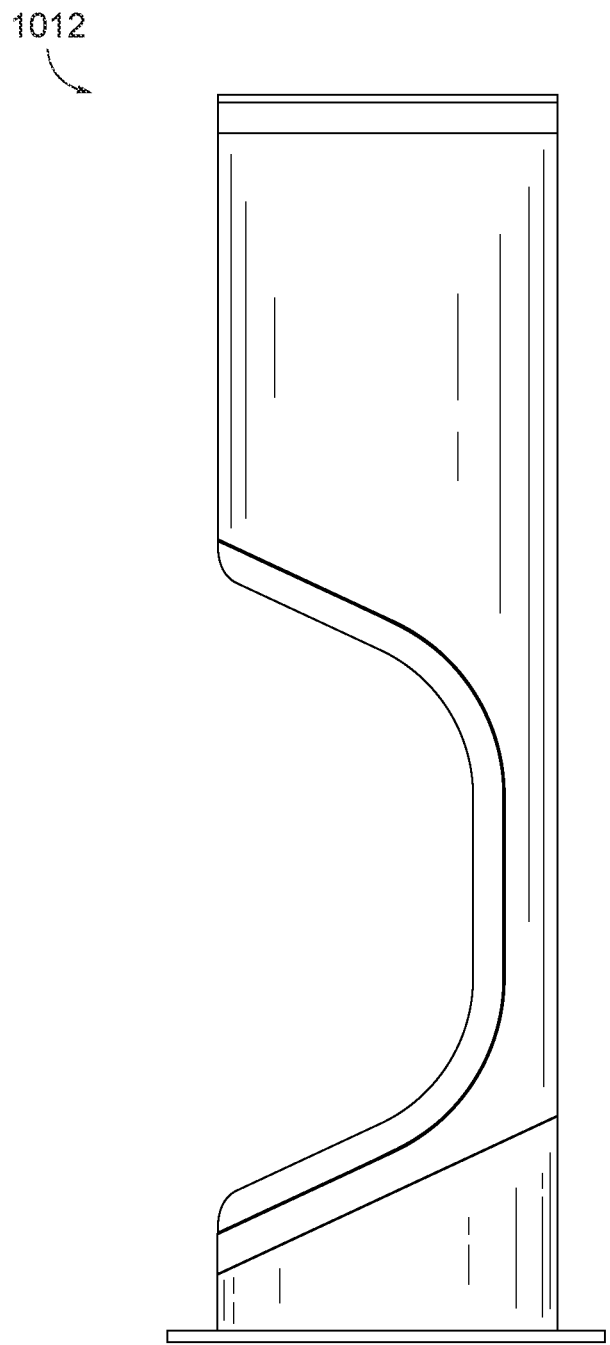
FIG. 10F illustratively depicts the right view of a modular fluid dispensing system with a floor base unit, in accordance with an implementation of the disclosure.

FIG. 10F illustratively depicts the right view of a modular fluid dispensing system with a floor base unit 1012.

Figure 10G:
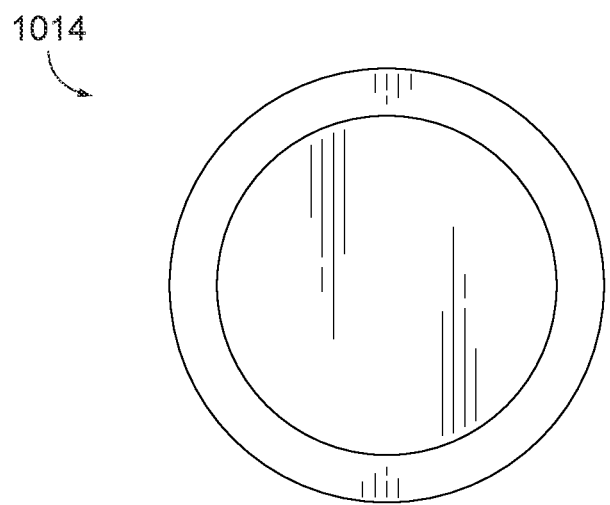
FIG. 10G illustratively depicts the top view of a modular fluid dispensing system with a floor base unit, in accordance with an implementation of the disclosure.

FIG. 10G illustratively depicts the top view of a modular fluid dispensing system with a floor base unit 1014.

Figure 10H:
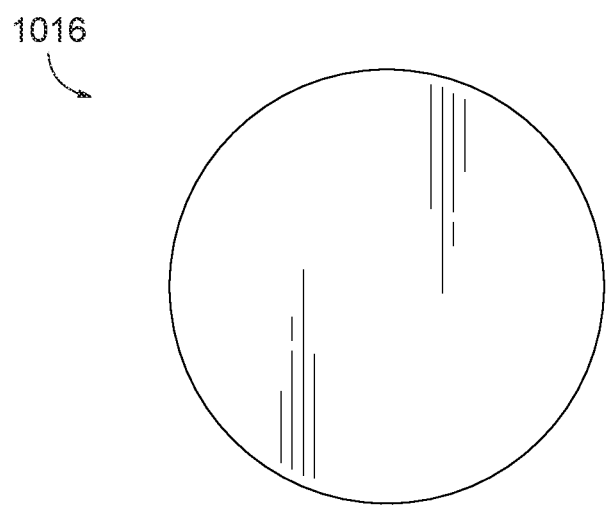
FIG. 10H illustratively depicts the bottom view of a modular fluid dispensing system with a floor base unit.

FIG. 10H illustratively depicts the bottom view of a modular fluid dispensing system with a floor base unit 1016.

The description of the modular fluid dispensing system with a desk base unit 700 in FIG. 7A applies to FIGS. 10A-10H.

Figure 11A:
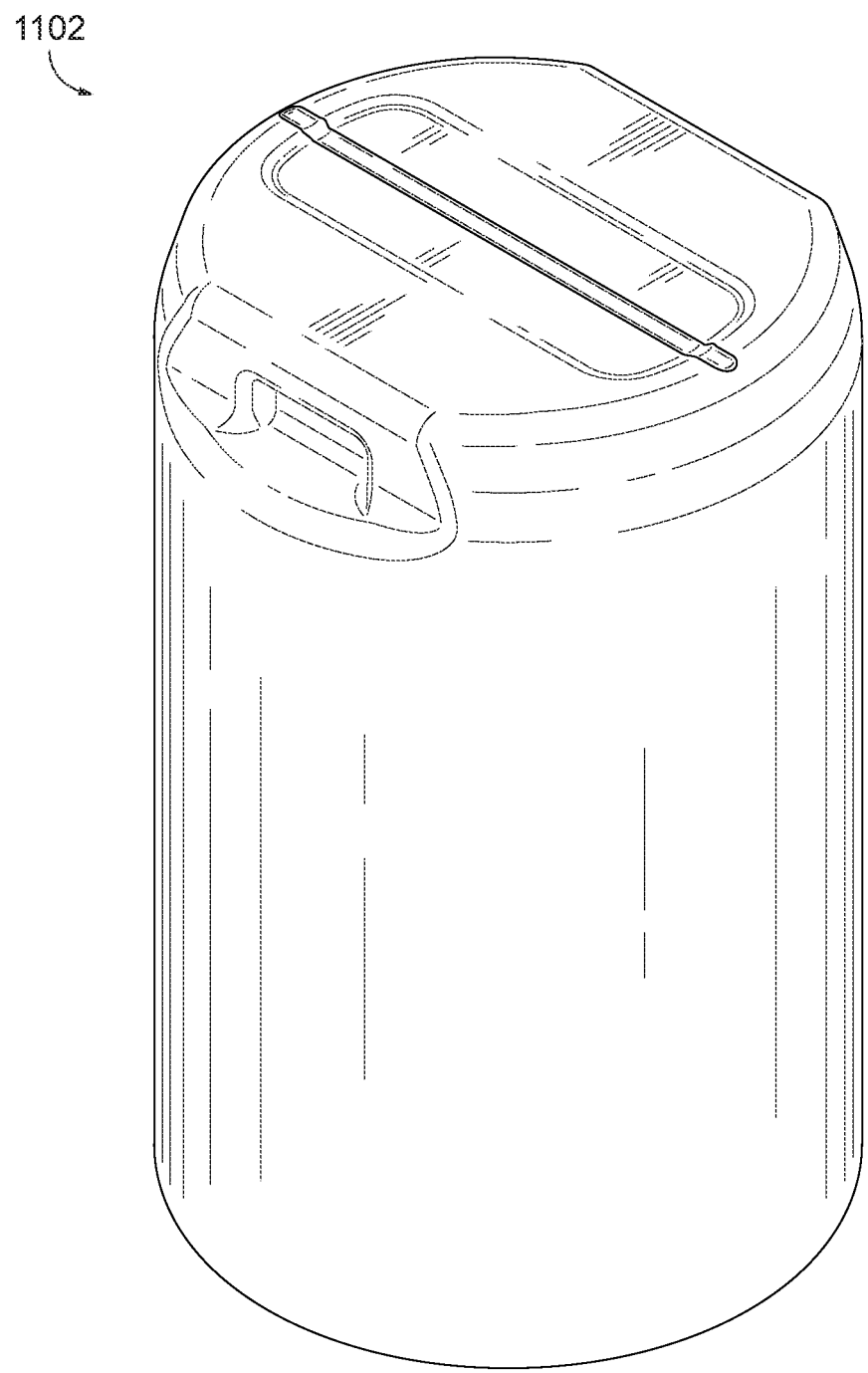
FIG. 11A illustratively depicts the front isometric view of a bottle, in accordance with an implementation of the disclosure.

FIG. 11A illustratively depicts the front isometric view of a bottle 1102.

Figure 11B:
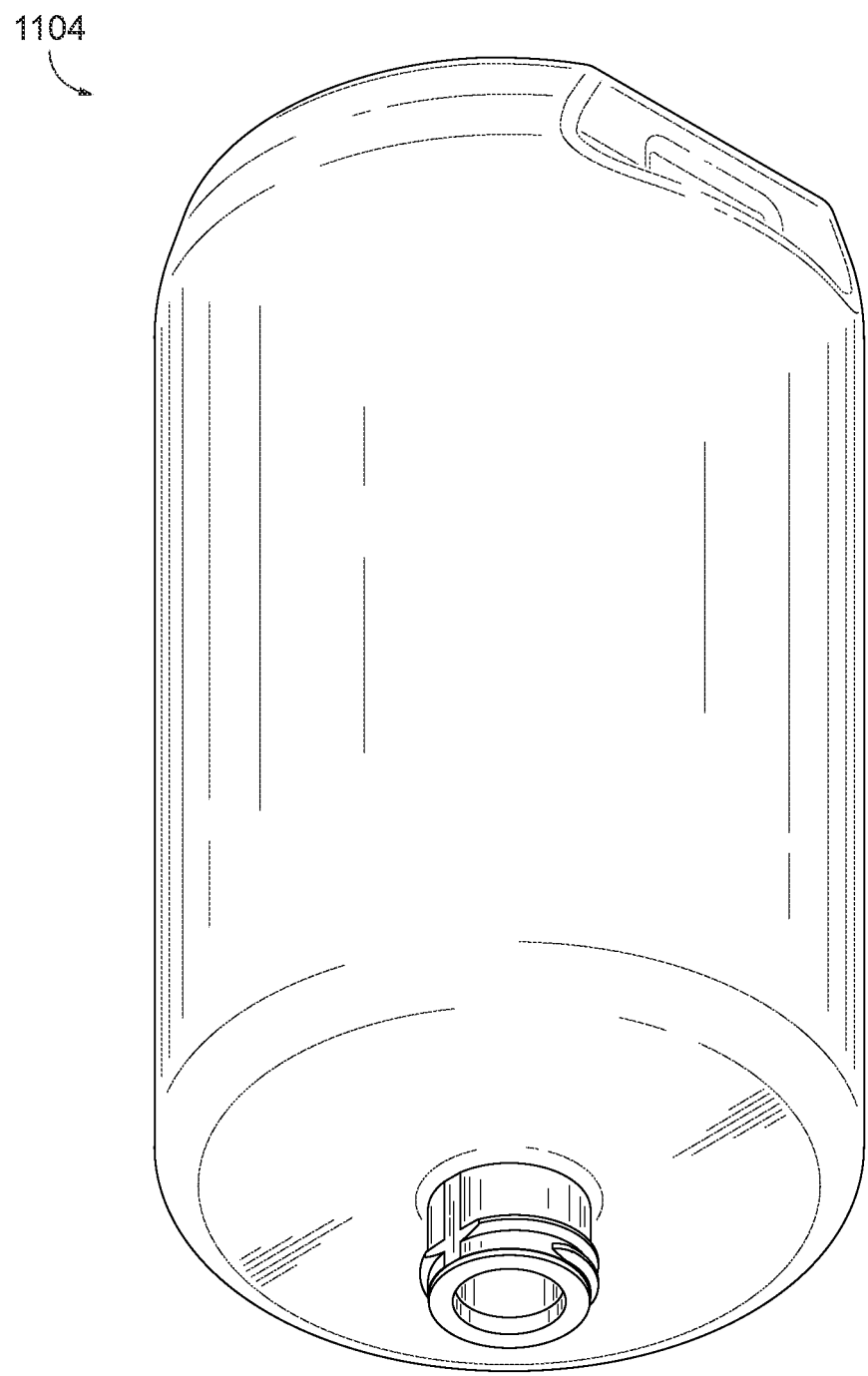
FIG. 11B illustratively depicts the back isometric view of a bottle, in accordance with an implementation of the disclosure.

FIG. 11B illustratively depicts the back isometric view of a bottle 1104.

Figure 11C:
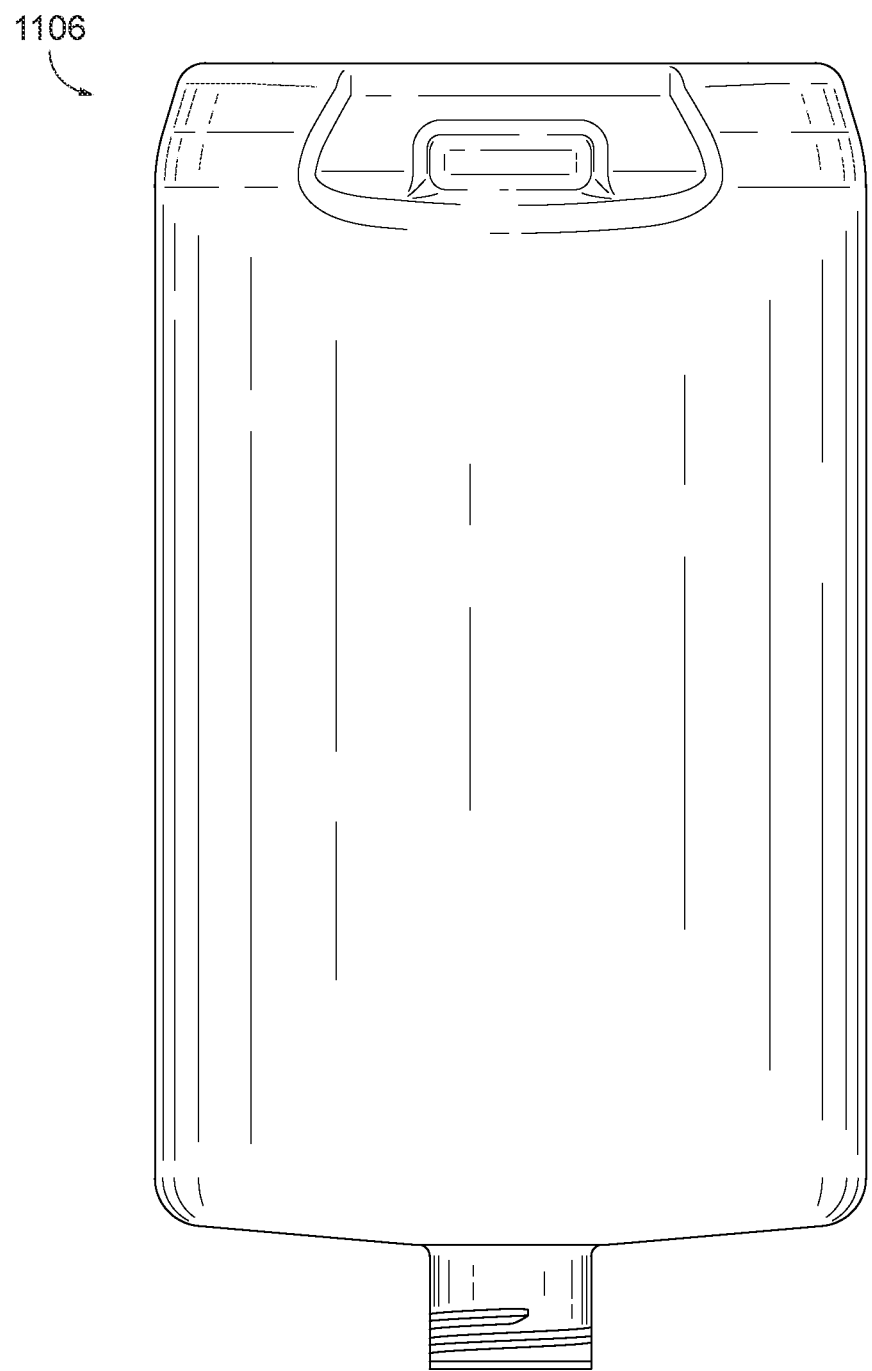
FIG. 11C illustratively depicts the front view of a bottle, in accordance with an implementation of the disclosure.

FIG. 11C illustratively depicts the front view of a bottle 1106.

Figure 11D:
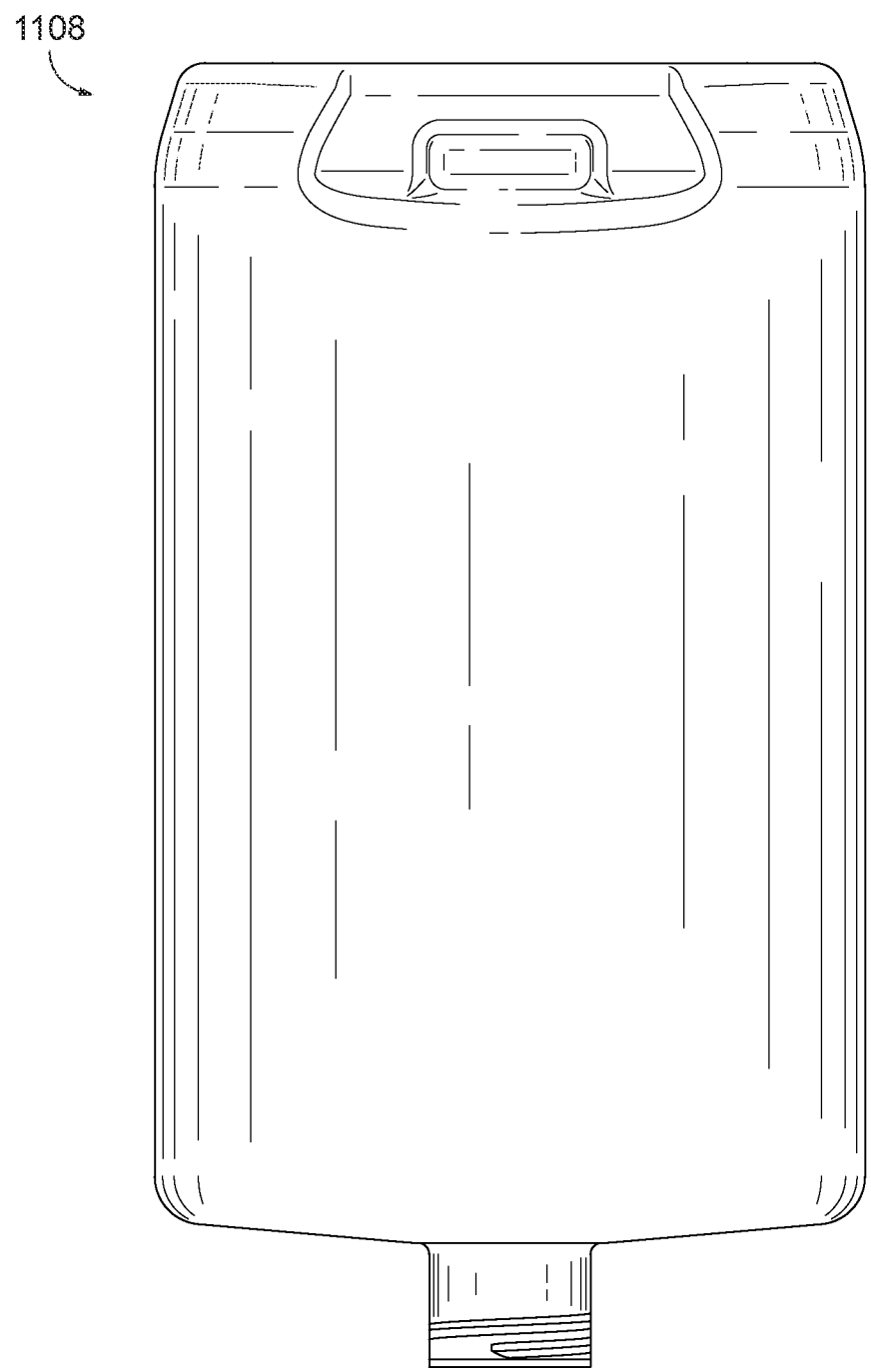
FIG. 11D illustratively depicts the back view of a bottle, in accordance with an implementation of the disclosure.

FIG. 11D illustratively depicts the back view of a bottle 1108.

Figure 11E:
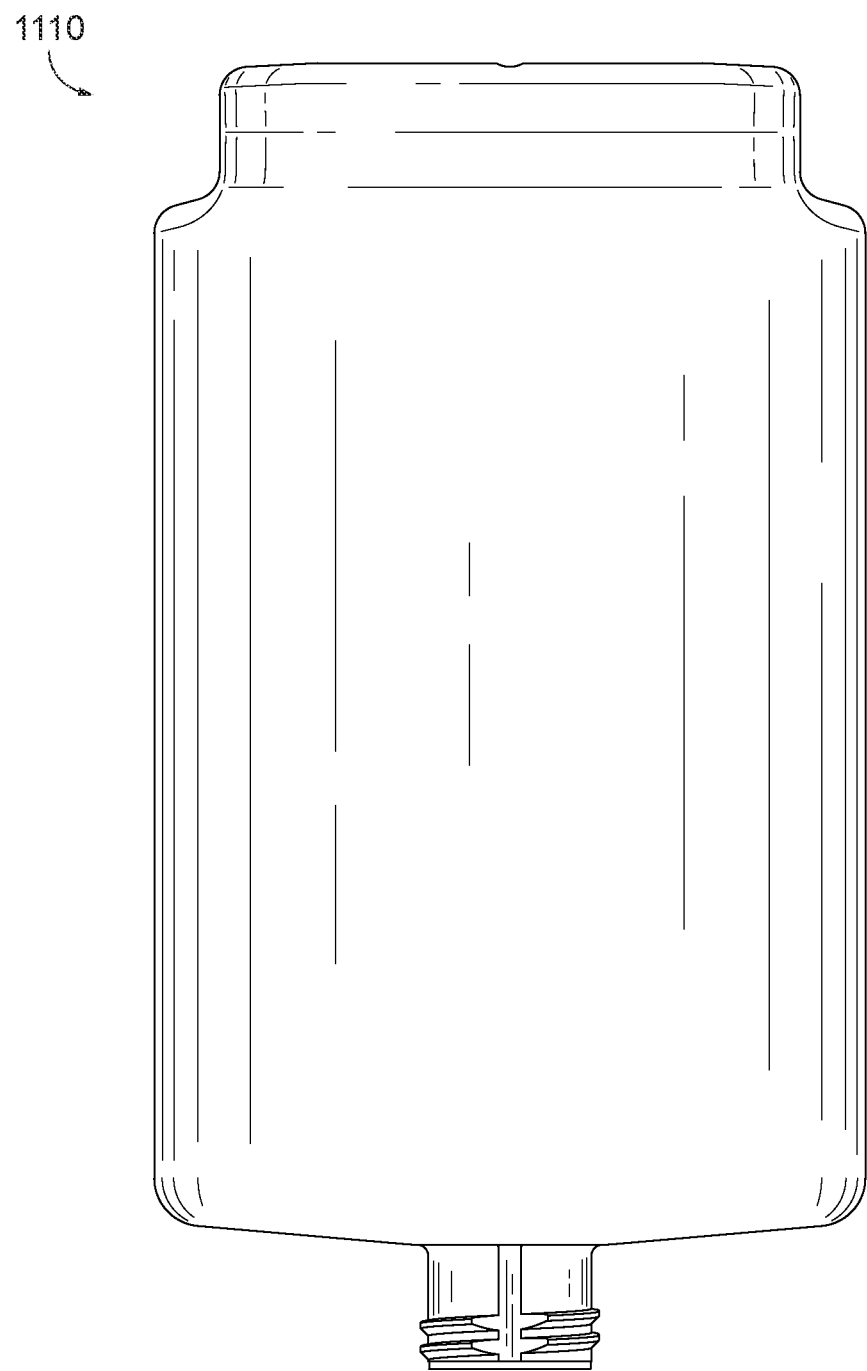
FIG. 11E illustratively depicts the left view of a bottle, in accordance with an implementation of the disclosure.

FIG. 11E illustratively depicts the left view of a bottle 1110.

Figure 11F:
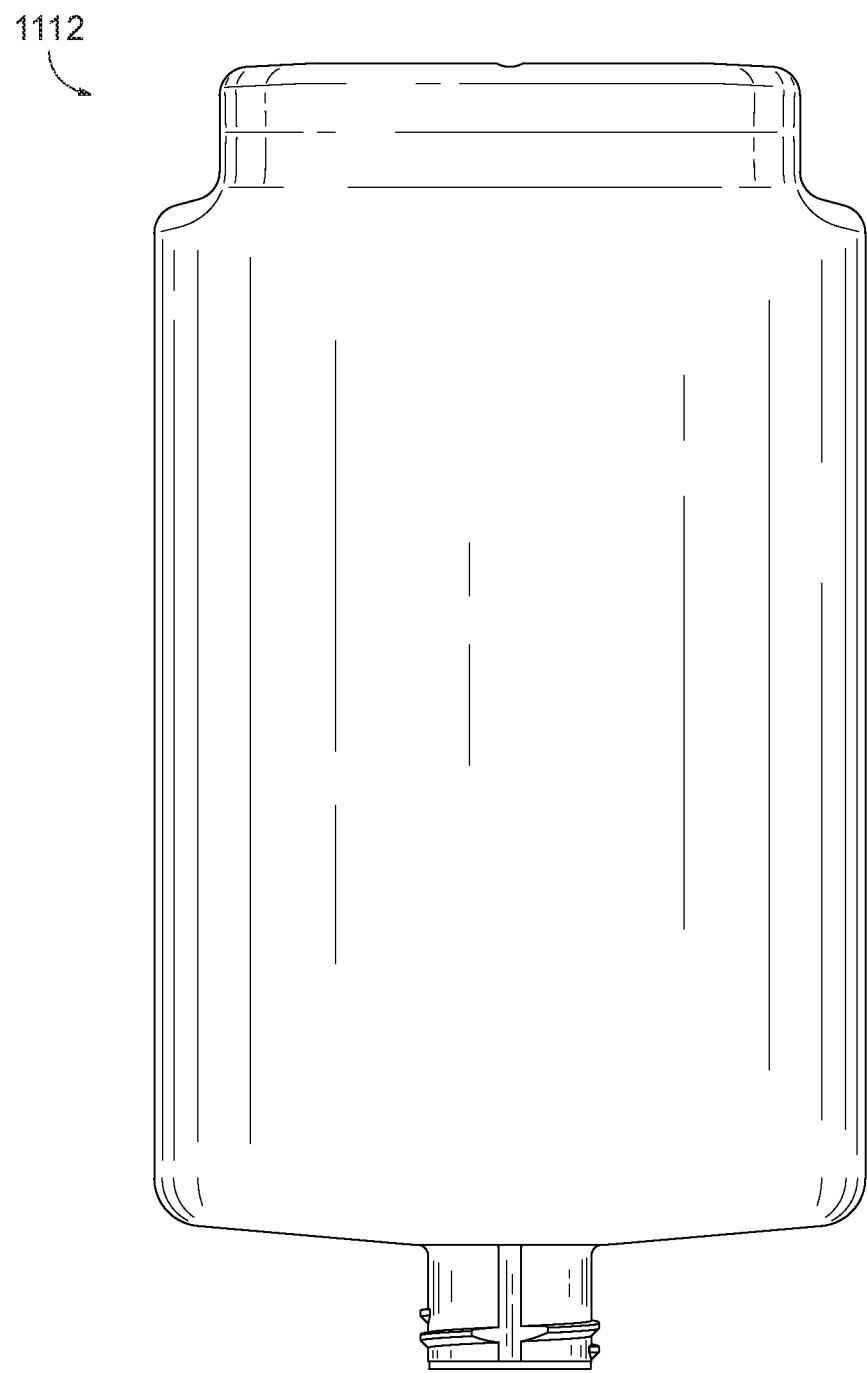
FIG. 11F illustratively depicts the right view of a bottle, in accordance with an implementation of the disclosure.

FIG. 11F illustratively depicts the right view of a bottle 1112.

Figure 11G:
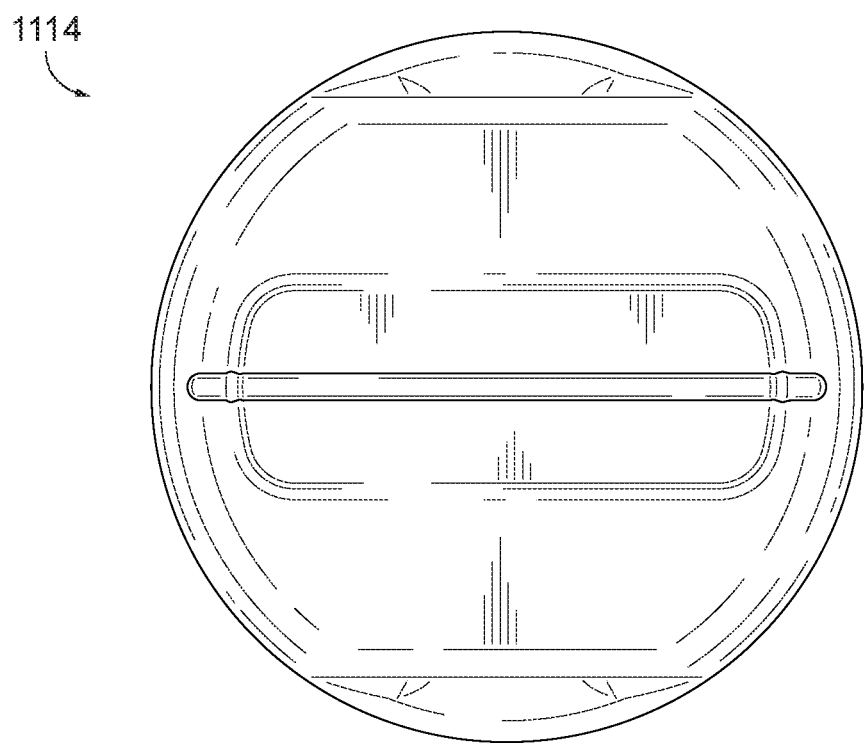
FIG. 11G illustratively depicts the top view of a bottle, in accordance with an implementation of the disclosure.

FIG. 11G illustratively depicts the top view of a bottle 1114.

Figure 11H:
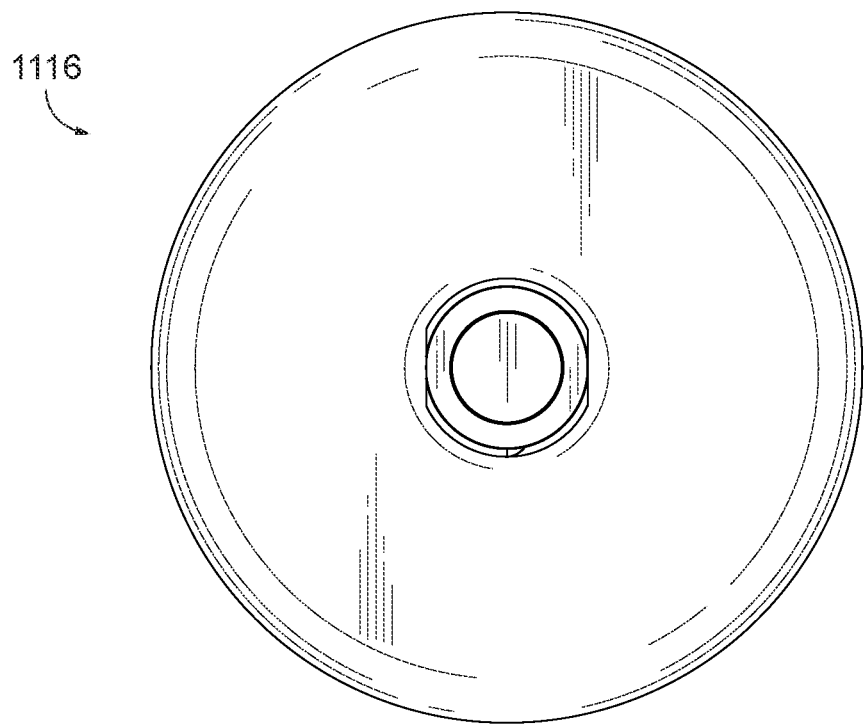
FIG. 11H illustratively depicts the bottom view of a bottle, in accordance with an implementation of the disclosure.

FIG. 11H illustratively depicts the bottom view of a bottle 1116.

The description of the bottle 600 in FIG. 6 applies to FIGS. 11A-11H.

As described above, the modular fluid dispensing system is advantageous over existing systems. The modular fluid dispensing system includes a rigid bottle and vacuum break port that provides ease of use and ease of refill. As the fluid in the rigid bottle is dispensed, the vacuum break port introduces air into the bottle to replace the volume of the dispensed fluid. A current sensor may be attached to a pump in the flow path of the fluid. When the rigid bottle contains only air, the current sensor detects a change in the current draw of the pump. The modular fluid dispensing system also includes lighting that may not only be aesthetically pleasing but also functional in nature.

Moreover, if a user wishes to receive a volume of hand sanitizing solution to sanitize their hands, the dispenser has an ergonomic shape that invites a user to place his/her hand in the correct location, includes a sensor to detect the presence of a hand of the user. In response to detecting a hand of a user, the sensor sends a signal to a pump, which initiates flow of the fluid from the rigid bottle to a nozzle and onto the hand of the user. If the rigid bottle contains only air and it is determined that the bottle needs to be replaced, the current sensor detects the change in current draw of the pump, and the dispenser may then alert the user that a refill is required.

The rigid bottle and vacuum break port may be utilized in combination to flush the dispenser in preparation for introducing a change in fluid. Dependent on the level of sensitivity of the new fluid to cross-contamination, the dispenser may be flushed in one of several configurations. For instance, a simple air flush may be accomplished by continuing to run the dispenser after the rigid bottle contains only air. In another instance, a more thorough flush may be accomplished by temporarily affixing a source of water to the vacuum break port and running the dispenser until only water is dispensed. In still another instance, a source of pressurized gas, such as carbon dioxide, argon, or nitrogen, may be at least temporarily affixed to the vacuum break port to accomplish an inert gas purge.

In addition, as the modular fluid dispensing system is modular, it can be wall mounted or placed as free-standing and it can easily toggle between various implementations. An attachment mechanism allows the modular fluid dispensing system to affix to a support structure.

While the implementations are susceptible to various modifications and alternative forms, specific examples thereof have been shown in the drawings and are herein described in detail. It should be understood, however, that these implementations are not to be limited to the particular form disclosed, but to the contrary, these implementations are to cover all modifications, equivalents, and alternatives falling within the spirit of the disclosure. Furthermore, any features, functions, steps, or elements of the implementations may be recited in or added to the claims, as well as negative limitations that define the inventive scope of the claims by features, functions, steps, or elements that are not within that scope.

What is claimed is:

1. A modular fluid dispensing system comprising:
 a bottle comprising two concave surfaces, each concave surface configured to enable a user to grip the bottle with a finger;
 a body comprising:
  a bottle housing configured to house the bottle, wherein the bottle housing comprises a fluid port to permit flow of a fluid at least one of in or out of the bottle, the bottle housing further comprising a threaded fastener for forming a fluid seal between the bottle and the fluid port, the threaded fastener comprising a puncturing taper configured to puncture a membrane seal of the bottle;
  a dispenser underneath the bottle housing, wherein the dispenser is configured to dispense the fluid, the dispenser comprising an electrical power supply to power the dispenser, a sensor configured to sense a body part of a user and generate a command, a pump configured to initiate flow of the fluid in response to receiving the command from the sensor, a nozzle, a tubing system configured to form a fluid connection between the fluid port, the pump, and the nozzle, wherein the tubing system comprises:
   a vacuum break port configured to permit air into the bottle such that as the pump initiates flow of the fluid from the bottle and out through the nozzle the fluid flowing out of the bottle is replaced with the air, the vacuum break port comprising a first opening configured to permit ingress of the fluid and a second opening connected to a first opening of the tubing system, wherein the tubing system comprises a second opening connected to an opening of a fluid channel in the fluid port which forms a continuous fluid connection between the first opening of the vacuum break port and the bottle, and
   a one-way valve configured to prevent the fluid from flowing out of the vacuum break port, the one-way valve configured to open in response to pressure at the second opening of the one-way vacuum break port being greater than pressure inside the bottle and the one-way valve configured to remain shut otherwise, the one-way valve comprising a spring to prevent flow until a minimum differential pressure is achieved, wherein the one-way valve is one of: located within a flow path between the second opening of the vacuum break port and the opening of the fluid channel in the fluid port or integrated with one of the vacuum break port or the fluid port; and
  an attachment mechanism on an exterior surface of the body configured to reversibly affix the body to a support structure configured to support the modular fluid dispensing system.

2. The modular fluid dispensing system of claim 1, wherein the bottle housing further comprises a removable lid, wherein the removable lid is configured such that the removable lid couples to the bottle housing in response to rotating the removable lid in a counter-clockwise direction.

3. The modular fluid dispensing system of claim 1, wherein the fluid comprises at least one of a sanitizing solution, a liquid soap, a lotion, a shampoo, a conditioner, a beverage, or a condiment.

4. The modular fluid dispensing system of claim 1, wherein the body comprises a light emitting diode.

5. The modular fluid dispensing system of claim 1, wherein the electrical power supply comprises an electric battery compartment configured to house an electrical battery or an adapter configured to connect to an electrical receptacle.

6. The modular fluid dispensing system of claim 1, wherein the sensor is configured to detect light.

7. The modular fluid dispensing system of claim 1, wherein the support structure comprises at least one of a wall mount, a base configured to be placed on a table, or a base configured to be placed on a floor.

8. A fluid dispensing system comprising:
 a bottle comprising two concave surfaces, each concave surface configured to enable a user to grip the bottle with a finger;
 a body comprising:
  a bottle housing configured to house the bottle, wherein the bottle housing comprises a fluid port to permit flow of a fluid into or out of the bottle, the bottle housing further comprising a threaded fastener for forming a fluid seal between the bottle and the fluid port, the threaded fastener comprising a puncturing taper configured to puncture a membrane seal of the bottle;
  a dispenser underneath the bottle housing, wherein the dispenser is configured to dispense the fluid, the dispenser comprising an electrical power supply to power the dispenser, a sensor configured to sense a body part of a user and generate a command, a pump configured to initiate flow of the fluid in response to receiving the command from the sensor, a nozzle, a tubing system configured to form a fluid connection between the bottle, the pump, and the nozzle, wherein the tubing system comprises:
   a vacuum break port configured to permit air into the bottle such that as the pump initiates flow of the fluid from the bottle and out through the nozzle the fluid flowing out of the bottle is replaced with the air, the vacuum break port comprising a first opening configured to permit ingress of the fluid and a second opening connected to a first opening of the tubing system, wherein the tubing system comprises a second opening connected to an opening of a fluid channel in the fluid port which forms a continuous fluid connection between the first opening of the vacuum break port and the bottle, and a one-way valve configured to prevent the fluid from flowing out of the vacuum break port, the one-way valve configured to open in response to pressure at the second opening of the one-way vacuum break port being greater than pressure inside the bottle and the one-way valve configured to remain shut otherwise, the one-way valve comprising a spring to prevent flow until a minimum differential pressure is achieved, wherein the one-way valve is one of: located within a flow path between the second opening of the vacuum break port and the opening of the fluid channel in the fluid port or integrated with one of the vacuum break port or the fluid port; and wherein the threaded fastener comprises one of a first male connection or a first female connection configured to couple to one of a second male or a second female connection of the bottle at a thread angle.

9. The fluid dispensing system of claim 8, wherein the thread angle ranges between 2 and 12 degrees.

10. A modular fluid dispensing system comprising:

a support structure configured to support the modular fluid dispensing system;

a bottle comprising two concave surfaces, each concave surface configured to enable a user to grip the bottle with a finger;

a body comprising:
  a bottle housing configured to house the bottle, wherein the bottle housing comprises a fluid port to permit flow of a fluid into or out of the bottle, the bottle housing further comprising a threaded fastener for forming a fluid seal between the bottle and the fluid port, the threaded fastener comprising a puncturing taper configured to puncture a membrane seal of the bottle;
  a dispenser underneath the bottle housing, wherein the dispenser is configured to dispense the fluid, the dispenser comprising an electrical power supply to power the dispenser, a sensor configured to sense a body part of a user and generate a command, a pump configured to initiate flow of the fluid in response to receiving the command from the sensor, a nozzle, a tubing system configured to form a fluid connection between the bottle, the pump, and the nozzle, wherein the tubing system comprises:
    a vacuum break port configured to permit air into the bottle such that as the pump initiates flow of the fluid from the bottle and out through the nozzle the fluid flowing out of the bottle is replaced with the air, the vacuum break port comprising a first opening configured to permit ingress of the fluid and a second opening connected to a first opening of the tubing system, wherein the tubing system comprises a second opening connected to an opening of a fluid channel in the fluid port which forms a continuous fluid connection between the first opening of the vacuum break port and the bottle,
    a one-way valve configured to prevent the fluid from flowing out of the vacuum break port, the one-way valve configured to open in response to pressure at the second opening of the one-way vacuum break port being greater than pressure inside the bottle and the one-way valve configured to remain shut otherwise, the one-way valve comprising a spring to prevent flow until a minimum differential pressure is achieved, wherein the one-way valve is one of: located within a flow path between the second opening of the vacuum break port and the opening of the fluid channel in the fluid port or integrated with one of the vacuum break port or the fluid port; and an attachment mechanism on an exterior surface of the body configured to reversibly affix the body to either or both of a support structure or at least one of a plurality of base units configured to support the modular fluid dispensing system.

11. The modular fluid dispensing system of claim 10, wherein the fluid comprises at least one of a sanitizing solution, a liquid soap, a lotion, a shampoo, a conditioner, a beverage, or a condiment.

12. The modular fluid dispensing system of claim 10, wherein the attachment mechanism comprises one of a first male connection or a first female connection configured to couple to one of a second male or a second female connection of a base unit at a thread angle.

13. The modular fluid dispensing system of claim 10, wherein the electrical power supply comprises an electric battery compartment configured to house an electrical battery or an adapter configured to connect to an electrical receptacle.

14. The modular fluid dispensing system of claim 10, wherein the dispenser comprises a drip tray.

15. The modular fluid dispensing system of claim 10, wherein the sensor is configured to detect light.

16. The modular fluid dispensing system of claim 10, wherein the threaded connection comprises a thread angle, wherein the thread angle ranges between 2 and 12 degrees.

17. The modular fluid dispensing system of claim 10, wherein the dispenser further comprises a second sensor configured to detect movement of the fluid.

18. The modular fluid dispensing system of claim 10, wherein the dispenser further comprises a second sensor configured to detect electrical current flowing through a motor of the pump.

19. The modular fluid dispensing system of claim 10, wherein the dispenser comprises a selector switch, wherein the command received by the pump instructs the pump to dispense the fluid in response to a selection of a position of the selector switch.

20. The modular fluid dispensing system of claim 1, wherein the one-way valve comprises a first one-way valve, the system further comprising:

a second one-way valve placed adjacent the nozzle and integrated between the second opening of the fluid channel in the fluid port and the pump to prevent contamination of the fluid remaining in the bottle due to backflow.

\* \* \* \* \*